(12) United States Patent
Bernstein et al.

(10) Patent No.: US 9,631,226 B2
(45) Date of Patent: Apr. 25, 2017

(54) AGENTS PROVIDING CONTROLS AND STANDARDS FOR IMMUNOPRECIPITATION ASSAYS

(71) Applicant: The General Hospital Corporation, Boston, MA (US)

(72) Inventors: Bradley E. Bernstein, Cambridge, MA (US); Alon Goren, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 30 days.

(21) Appl. No.: 14/855,664

(22) Filed: Sep. 16, 2015

(65) Prior Publication Data

US 2016/0068885 A1 Mar. 10, 2016

Related U.S. Application Data

(60) Division of application No. 13/853,216, filed on Mar. 29, 2013, now Pat. No. 9,175,043, which is a continuation-in-part of application No. PCT/US2011/053950, filed on Sep. 29, 2011.

(60) Provisional application No. 61/387,673, filed on Sep. 29, 2010.

(51) Int. Cl.
*C12Q 1/68* (2006.01)
*C07K 9/00* (2006.01)
*G01N 33/68* (2006.01)

(52) U.S. Cl.
CPC .............. *C12Q 1/6804* (2013.01); *C07K 9/00* (2013.01); *C12Q 1/68* (2013.01); *G01N 33/6875* (2013.01); *C12Q 2525/203* (2013.01); *C12Q 2600/166* (2013.01)

(58) Field of Classification Search
None
See application file for complete search history.

(56) References Cited

U.S. PATENT DOCUMENTS

| 5,723,598 | A | 3/1998 | Lerner et al. |
|---|---|---|---|
| 7,303,866 | B2 | 12/2007 | Halazonetis et al. |
| 9,175,043 | B2 | 11/2015 | Bernstein et al. |
| 2004/0214758 | A1 | 10/2004 | Meyers et al. |
| 2005/0089880 | A1 | 4/2005 | Jenuwein et al. |
| 2006/0084078 | A1 | 4/2006 | Zhao |
| 2006/0134714 | A1 | 6/2006 | Sundararajan et al. |
| 2007/0141583 | A1 | 6/2007 | Li et al. |
| 2009/0035836 | A1 | 2/2009 | Datta et al. |
| 2009/0149343 | A1 | 6/2009 | Nightingale |

FOREIGN PATENT DOCUMENTS

| WO | WO 2005/054461 A2 | 6/2005 |
|---|---|---|
| WO | WO 2009/151491 A2 | 12/2009 |
| WO | WO 2010/094027 A1 | 8/2010 |

OTHER PUBLICATIONS

Amit et al., Unbiased reconstruction of a mammalian transcriptional network mediating pathogen responses. Science. Oct. 9, 2009;326(5950):257-63. doi: 10.1126/science.1179050. Epub Sep. 3, 2009.
Bailey et al., Combining evidence using p-values: application to sequence homology searches. Bioinformatics. 1998;14(1):48-54.
Bailey et al., Fitting a mixture model by expectation maximization to discover motifs in biopolymers. Proc Int Conf Intell Syst Mol Biol. 1994;2:28-36.
Barish et al., Bcl-6 and NF-kappaB cistromes mediate opposing regulation of the innate immune response. Genes Dev. Dec. 15, 2010;24(24):2760-5. doi: 10.1101/gad.1998010. Epub Nov. 24, 2010.
Barski et al., High-resolution profiling of histone methylations in the human genome. Cell. May 18, 2007;129(4):823-37.
Berger et al., Variation in homeodomain DNA binding revealed by high-resolution analysis of sequence preferences. Cell. Jun. 27, 2008;133(7):1266-76. doi: 10.1016/j.cell.2008.05.024.
Bossard et al., GATA transcription factors as potentiators of gut endoderm differentiation. Development. Dec. 1998;125(24):4909-17.
Capaldi et al., Structure and function of a transcriptional network activated by the MAPK Hog1. Nat Genet. Nov. 2008;40(11):1300-6. doi: 10.1038/ng.235. Epub Oct. 19, 2008.
Cirillo et al., An early developmental transcription factor complex that is more stable on than on free DNA. Mol Cell. Dec. 1999;4(6):961-9.
Cirillo et al., Opening of compacted chromatin by early developmental transcription factors HNF3 (FoxA) and GATA-4. Mol Cell. Feb. 2002;9(2):279-89.
Davidson, Emerging properties of animal gene regulatory networks. Nature. Dec. 16, 2010;468(7326):911-20. doi: 10.1038/nature09645.
Davis et al., Expression of a single transfected cDNA converts fibroblasts to myoblasts. Cell. Dec. 24, 1987;51(6):987-1000.
De Santa et al., A large fraction of extragenic RNA pol II transcription sites overlap enhancers. PLoS Biol. May 11, 2010;8(5):e1000384. doi: 10.1371/journal.pbio.1000384.
Flicek et al., Ensembl's 10th year. Nucleic Acids Res. Jan. 2010;38(Database issue):D557-62. doi: 10.1093/nar/gkp972. Epub Nov. 11, 2009.
Foster et al., Gene-specific control of inflammation by TLR-induced chromatin modifications. Nature. Jun. 21, 2007;447(7147):972-8. Epub May 30, 2007. Erratum in: Nature. Jan. 3, 2008;451(7174):102.
Fujita et al., The UCSC Genome Browser database: update 2011. Nucleic Acids Res. Jan. 2011;39(Database issue):D876-82. doi: 10.1093/nar/gkq963. Epub Oct. 18, 2010.
Geiss et al., Direct multiplexed measurement of gene expression with color-coded probe pairs. Nat Biotechnol. Mar. 2008;26(3):317-25. doi: 10.1038/nbt1385. Epub Feb. 17, 2008. Corrigendum: Nat Biotechnol. Jun. 2008;26(6):1.

(Continued)

*Primary Examiner* — Jacob Cheu
(74) *Attorney, Agent, or Firm* — Wolf, Greenfield & Sacks, P.C.

(57) ABSTRACT

Control agents for immunoprecipitation assays, methods of using the control agents and kits comprising the control agents are provided.

16 Claims, 6 Drawing Sheets

(56) References Cited

OTHER PUBLICATIONS

Gerstein et al., Integrative analysis of the Caenorhabditis elegans genome by the modENCODE project. Science. Dec. 24, 2010;330(6012):1775-87. doi: 10.1126/science.1196914. Epub Dec. 22, 2010. Erratum in: Science. Jan. 7, 2011;331(6013):30.
Ghisletti et al., Cooperative NCoR/SMRT interactions establish a corepressor-based strategy for integration of inflammatory and anti-inflammatory signaling pathways. Genes Dev. Mar. 15, 2009;23(6):681-93. doi: 10.1101/gad.1773109.
Graf et al., Forcing cells to change lineages. Nature. Dec. 3, 2009;462(7273):587-94. doi: 10.1038/nature08533.
Griffith et al., Open Regulatory Annotation Consortium. ORegAnno: an open-access community-driven resource for regulatory annotation. Nucleic Acids Res. Jan. 2008;36(Database issue):D107-13. Epub Nov. 15, 2007.
Grove et al., A multiparameter network reveals extensive divergence between C. elegans bHLH transcription factors. Cell. Jul. 23, 2009;138(2):314-27. doi: 10.1016/j.cell.2009.04.058.
Gupta et al., Quantifying similarity between motifs. Genome Biol. 2007;8(2):R24.
Guttman et al., Chromatin signature reveals over a thousand highly conserved large non-coding RNAs in mammals. Nature. Mar. 12, 2009;458(7235):223-7. doi: 10.1038/nature07672. Epub Feb. 1, 2009.
Harada et al., Structurally similar but functionally distinct factors, IRF-1 and IRF-2, bind to the same regulatory elements of IFN and IFN-inducible genes. Cell. Aug. 25, 1989;58(4):729-39.
Harbison et al., Transcriptional regulatory code of a eukaryotic genome. Nature. Sep. 2, 2004;431(7004):99-104.
Haring et al., Chromatin immunoprecipitation: optimization, quantitative analysis and data normalization. Plant Methods. Sep. 24, 2007;3:11. 16 pages.
Heinz et al., Simple combinations of lineage-determining transcription factors prime cis-regulatory elements required for macrophage and B cell identities. Mol Cell. May 28, 2010;38(4):576-89. doi: 10.1016/j.molcel.2010.05.004.
Hoffmann et al., Circuitry of nuclear factor kappaB signaling. Immunol Rev. Apr. 2006;210:171-86.
Hu et al., Genetic reconstruction of a functional transcriptional regulatory network. Nat Genet. May 2007;39(5):683-7. Epub Apr. 8, 2007.
Johnson et al., Genome-wide mapping of in vivo protein-DNA interactions. Science. Jun. 8, 2007;316(5830):1497-502. Epub May 31, 2007.
Katsnelson, Kicking off adaptive immunity: the discovery of dendritic cells. J Exp Med. Jul. 10, 2006;203(7):1622.
Kim et al., TopHat-Fusion: an algorithm for discovery of novel fusion transcripts. Genome Biol. Aug. 11, 2011;12(8):R72. doi: 10.1186/gb-2011-12-8-r72.
Kim et al., Widespread transcription at neuronal activity-regulated enhancers. Nature. May 13, 2010;465(7295):182-7. doi: 10.1038/nature09033. Epub Apr. 14, 2010.
Kozarewa et al., Amplification-free Illumina sequencing-library preparation facilitates improved mapping and assembly of (G+C)-biased genomes. Nat Methods. Apr. 2009;6(4):291-5. doi: 10.1038/nmeth.1311. Epub Mar. 15, 2009.
Lange-Zu Dohna et al., A CDE/CHR tandem element regulates cell cycle-dependent repression of cyclin B2 transcription. FEBS Lett. Nov. 3, 2000;484(2):77-81.
Langmead et al., Ultrafast and memory-efficient alignment of short DNA sequences to the human genome. Genome Biol. 2009;10(3):R25. doi: 10.1186/gb-2009-10-3-r25. Epub Mar. 4, 2009.
Laslo et al., Multilineage transcriptional priming and determination of alternate hematopoietic cell fates. Cell. Aug. 25, 2006;126(4):755-66.
Lenardo et al., NF-kappa B: a pleiotropic mediator of inducible and tissue-specific gene control. Cell. Jul. 28, 1989;58(2):227-9.
Li et al., Fast and accurate short read alignment with Burrows-Wheeler transform. Bioinformatics. Jul. 15, 2009;25(14):1754-60. doi: 10.1093/bioinformatics/btp324. Epub May 18, 2009.
Lupien et al., FoxA1 translates epigenetic signatures into enhancer-driven lineage-specific transcription. Cell. Mar. 21, 2008;132(6):958-70. doi: 10.1016/j.cell.2008.01.018.
McLean et al., Great improves functional interpretation of cis-regulatory regions. Nat Biotechnol. May 2010;28(5):495-501. doi: 10.1038/nbt.1630. Epub May 2, 2010.
Mikkelsen et al., Genome-wide maps of chromatin state in pluripotent and lineage-committed cells. Nature. Aug. 2, 2007;448(7153):553-60. Epub Jul. 1, 2007.
Nègre et al., A cis-regulatory map of the *Drosophila* genome. Nature. Mar. 24, 2011;471(7339):527-31. doi: 10.1038/nature09990.
Pabst et al., Transcriptional dysregulation during myeloid transformation in AML. Oncogene. Oct. 15, 2007;26(47):6829-37.
Peter et al., Evolution of gene regulatory networks controlling body plan development. Cell. Mar. 18, 2011;144(6):970-85. doi: 10.1016/j.cell.2011.02.017.
Pruitt et al., NCBI reference sequences (RefSeq): a curated non-redundant sequence database of genomes, transcripts and proteins. Nucleic Acids Res. Jan. 2007;35(Database issue):D61-5. Epub Nov. 27, 2006.
Rabani et al., Metabolic labeling of RNA uncovers principles of RNA production and degradation dynamics in mammalian cells. Nat Biotechnol. May 2011;29(5):436-42. doi: 10.1038/nbt.1861. Epub Apr. 24, 2011.
Rada-Iglesias et al., A unique chromatin signature uncovers early developmental enhancers in humans. Nature. Feb. 1, 2011;10;470(7333):279-83. doi: 10.1038/nature09692. Epub Dec. 15, 2010.
Robinson et al., Integrative genomics viewer. Nat Biotechnol. Jan. 2011;29(1):24-6. doi: 10.1038/nbt.1754.
Roy et al., Identification of functional elements and regulatory circuits by *Drosophila* modENCODE. Science. Dec. 24, 2010;330(6012):1787-97. doi: 10.1126/science.1198374. Epub Dec. 22, 2010.
Segal et al., Module networks: identifying regulatory modules and their condition-specific regulators from gene expression data. Nat Genet. Jun. 2003;34(2):166-76.
Solomon et al., Formaldehyde-mediated DNA-protein crosslinking: a probe for in vivo chromatin structures. Proc Natl Acad Sci U S A. Oct. 1985;82(19):6470-4.
Thanos et al., The high mobility group protein HMG I(Y) is required for NF-kappa B-dependent virus induction of the human IFN-beta gene. Cell. Nov. 27, 1992;71(5):777-89.
Wallenstein et al., An approximation for the distribution of the scan statistic. Stat Med. Mar. 1987;6(2):197-207.
Weintraub et al., Activation of muscle-specific genes in pigment, nerve, fat, liver, and fibroblast cell lines by forced expression of MyoD. Proc Natl Acad Sci U S A. Jul. 1989;86(14):5434-8.
Yosef et al., Impulse control: temporal dynamics in gene transcription. Cell. Mar. 18, 2011;144(6):886-96. doi: 10.1016/j.cell.2011.02.015.
Zhou et al., In vivo reprogramming of adult pancreatic exocrine cells to beta-cells. Nature. Oct. 2, 2008;455(7213):627-32. doi: 10.1038/nature07314. Epub Aug. 27, 2008.
Zinzen et al., Combinatorial binding predicts spatio-temporal cis-regulatory activity. Nature. Nov. 5, 2009;462(7269):65-70. doi: 10.1038/nature08531.

AGENTS PROVIDING CONTROLS AND STANDARDS FOR IMMUNOPRECIPITATION ASSAYS

RELATED APPLICATIONS

This application is a divisional of U.S. application Ser. No. 13/853,216, filed Mar. 29, 2013, which a continuation-in-part of international application number PCT/US2011/053950, filed Sep. 29, 2011, which claims the benefit under 35 U.S.C. §119(e) of U.S. provisional application Ser. No. 61/387,673, filed Sep. 29, 2010, each of which is incorporated by reference herein in its entirety.

GOVERNMENT SUPPORT

This invention was made with government support under U54 HG004570 awarded by the National Institutes of Health and under U01 ES017155 awarded by the National Institutes of Health. The government has certain rights in the invention.

BACKGROUND OF INVENTION

Chromatin immunoprecipitation (ChIP) is a powerful tool for evaluating interaction of proteins with specific genomic DNA regions in vivo, to provide a better understanding of the mechanisms of gene regulation, DNA replication, and DNA repair. The ChIP technique involves fixative treatment of live cells with formaldehyde to chemically cross-link DNA-bound proteins. The cells are then lysed, and the chromatin is sheared mechanically or enzymatically, in order to reduce fragment size and increase resolution. The resultant sheared complexes are then immuno-precipitated with antibodies specific to the protein of interest, and the DNA fragments are analyzed, e.g. using real time PCR, sequencing, or microarray hybridization. The ChIP protocol was introduced in 1988 (Solomon M J et al. Cell. 1988 53(6):937-47). Its power and widespread use has increased significantly with the incorporation of nucleic acid detection assays such as microarrays and sequencing that have enabled the method to be scaled genome-scale or genome-wide.

SUMMARY OF INVENTION

Aspects of the invention relate to control agents for immunoprecipitation (IP) assays. In certain embodiments, the immunoprecipitation assay is a chromatin immunoprecipitation assay (ChIP). The control agents provided herein comprise a polypeptide segment providing an antigen and a oligonucleotide segment comprising a unique sequence that allows identification of the control agent. The two segments are linked together by a linker molecule. The antigen may comprise exclusively unmodified amino acids or one or more modified amino acids. In certain embodiments, amino acid modifications are those common during post-translational protein modification in vivo, such as acetylation, methylation (e.g. mono-, di-, tri-), phosphorylation, ubiquitination (e.g. mono-, di-, tri-, poly-), sumoylation, ADP-ribosylation, citullination, and cis-trans isomerization. In other embodiments, antigens may comprise specific mutations of a wild-type amino acid sequence, such as point mutations. In yet other embodiments, antigens may comprise exclusively wild-type amino acid sequence. The polypeptide segment comprising the antigen may comprise amino acid fragments derived from histone proteins or non-histone proteins. In certain embodiments, the polypeptide segment comprising the antigen consists of at least 5 amino acids. In certain embodiments, the oligonucleotide segment comprising the unique identifier consists of at least 10 nucleotides. In certain embodiments, the oligonucleotide segment further comprises one or more amplification sequences.

Further provided herein are methods of using the control agents in IP assays, methods of using the control agents in screening antibodies for suitability in IP assays, and methods of using the control agents to normalize data obtained from performing ChIP assays.

Further provided herein are kits comprising the control agents described herein for use in IP assays.

In certain aspects the invention provides polypeptide-oligonucleotide conjugate of the formula:

A-L-N, wherein A is a polypeptide comprising 5 amino acids, L is a linker, and N is an oligonucleotide comprising 10 nucleotides, wherein the sequence of nucleotides of N uniquely identifies an amino acid sequence and/or amino acid modification of A. In certain embodiments, A is 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 amino acids. In certain embodiments, A is 5-15, 5-25, 5-50, 5-100, 5-250, 5-500, 5-1000, 5-2500, 5-5000, 5-10,000, 5-25,000, or 5-50,000 amino acids.

In certain embodiments, A comprises a modified amino acid. In certain embodiments, the modification is a post-translational modification. In such embodiments, the modification may be selected from the group consisting of acetylation, methylation (mono-, di-, tri-), phosphorylation, ubiquitination (mono-, di-, tri-, poly-), sumoylation, ADP-ribosylation, citullination, biotinylation, and cis-trans isomerization.

In certain embodiments, A comprises an amino acid sequence derived from a histone protein selected from the group consisting of histone H1, H2A, H2AX, H2B, H3, H4. In certain embodiments, the amino acid sequence is derived from the amino terminus, whereas in other embodiments, the amino acid sequence is derived from the carboxyl terminus. In certain embodiments, A comprises 1, 2, 3, 4, 5, 6, 7, 8, 9, 10, 11, 12, 13, 14, 15, 16, 18, 19, 20, 21, 22, 23, 24, 25, 26, 27, 28, 29, 30, 31, 32, 33, 34, 35, or 36 amino acids of any one sequence selected from the group consisting of SGRGKQGCKARAK (SEQ ID NO: 1), VLLPKKTESHHKAKGK (SEQ ID NO: 2), PEPAKSAPAPKKGSKKAVTK (SEQ ID NO: 3), AVSEGTKAVTKYTSSK (SEQ ID NO: 4), ARTKQTARKSTGGKAPRKQLATKAARKSAPATGGVK (SEQ ID NO: 5), QRLVREIAQDFKTDLRFQSSAVMALQEA (SEQ ID NO: 6), SGRGKGGKGLGKGGAKRHRKVLRDNIQGITKPAIRRLA (SEQ ID NO: 7) and alterations thereof, selected from: a conservative amino acid exchange, a non-conservative amino acid exchange, and/or an amino acid exchange of a natural amino acid to a non-natural amino acid. In certain embodiments, the altered amino acid sequence is 90%, 95%, 98%, or 99% identical to one of the amino acid sequences set forth in SEQ ID NOs:

1-7. In certain embodiments, the amino acid sequence is derived from a histone of a mammal, a fish, a yeast, a plant, an insect, or a nematode.

In certain embodiments, A comprises:

$$X_nY[M]X_n,$$

wherein X is an amino acid, n is a number of amino acids, Y is a modified amino acid, M is a modification. In such embodiments, n is 0-15, 0-25, 0-50, 0-100, 0-150, 0-250, 0-500, 0-1000, 0-2500, 0-5000, 0-10,000, 0-25,000, or 0-50,000 amino acids. In such embodiments, M is selected from the group consisting of H1 (phospho S1+T3), H1 (phospho S35), H1 (acetyl K63); H2A (asymmetric di methyl R3), H2A (symmetric di methyl R3), H2A (acetyl K5), H2A (mono methyl R17), H2A (symmetric di methyl R77), H2A (Hydroxy P26), H2A (mono methyl K125), H2A (tri methyl K125), H2A (mono methyl K127), H2A (tri methyl K127), H2A (phospho S129); H2B (acetyl K5), H2B (di methyl K5), H2B (Hydroxy P10), H2B (di methyl K43); H3 (mono methyl R2), H3 (citrulline 2+8+17), H3 (mono methyl K4), H3 (di methyl K4), H3 (tri methyl K4), H3 (di+tri methyl K4), H3 (acetyl K9), H3 (acetyl K9, phospho S10), H3 (mono methyl K9), H3 (di methyl K9), H3 (tri methyl K9), H3 (phospho S10), H3 (asymmetric di methyl R17), H3 (acetyl K18), H3 (acetyl K27), H3 (di methyl K27), H3 (tri methyl K27), H3 (mono methyl K27, tri methyl K27+K4), H3 (mono methyl K36), H3 (tri methyl K36), H3 (Hydroxy P38), H3 (mono methyl K79), H3 (di methyl K79), H3 (tri methyl K79), H3 (mono+di+tri methyl K79), H3 (Hydroxy P121), H3 (tri methyl K122); H4 (symmetric di methyl R3), H4 (acetyl K8), H4 (acetyl K12), H4 (mono methyl K20), H4 (tri methyl K20), H4 (phospho T30), H4 (Hydroxy P32), H4 (tri methyl K59), H4 (phospho T80), H4 (acetyl K91), and H4 (phospho T96).

In certain embodiments, N of the polypeptide-oligonucleotide conjugate of any one of the preceding embodiments is 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 nucleotides. In certain embodiments, N is 10-25, 10-50, 10-100, 10-250, 10-500, 10-1000, 10-2500, 10-5000, 10-10,000, 10-25,000, 10-50,000 or 10-100,000 nucleotides.

In certain embodiments, N comprises a nucleotide sequence U that uniquely identifies an amino acid sequence and/or amino acid modification of A. In certain embodiments, the unique nucleotide sequence U consists of about 20, about 30, about 40, about 50, about 60, about 70, about 80, about 90, or about 100 nucleotides. In certain embodiments, the unique nucleotide sequence U is from 10 nucleotides to 500 nucleotides, from 20 to 200, from 30 to 300, from 40 to 400, from 15 to 150, from 50 to 100, from 25 to 75, or from 45 to 65 nucleotides. In certain embodiments, U is 10-1000, 10-2500, 10-5000, 10-10,000, 10-25,000, or 10-50,000 nucleotides.

In certain embodiments, N comprises:

$$x_nP1\text{-}U\text{---}P2x_n,$$

wherein x is any nucleotide, n is a number of nucleotides, P1 and P2 are primer sequences, and U is a unique sequence of nucleotides. In certain embodiments, the primer sequences P1 and P2 each are independently 15, 16, 17, 18, 19, 20, 21, 22, 23, 24, 25, 26, 27, 28, 29, 30, 31, 32, 33, 34, or 35 nucleotides. In certain embodiments, P1 and P2 each are independently 10-35, 10-40, 10-45, 10-50, 10-55, 10-60, 10-65, 10-70, 10-75, 10-100, 10-250, 10-500, or 10-1000 nucleotides. In certain embodiments, the primer sequences P1 and P2 each comprise 10 nucleotides. In certain embodiments, U is 10-50, 10-100, 10-250, 10-500, 10-1000, 10-2500, 10-5000, 10-10,000, 10-25,000, or 10-50,000 nucleotides. In certain embodiments, n is 0-15, 0-25, 0-50, 0-100, 0-150, 0-250, 0-500, 0-1000, 0-2500, 0-5000, 0-10,000, 0-25,000, or 0-50,000 amino acids.

In certain embodiments, N comprises:

$$x_nUx_n,$$

wherein x is any nucleotide, n is a number of nucleotides and U is a unique sequence of nucleotides. In certain embodiments, U is 10-50, 10-100, 10-250, 10-500, 10-1000, 10-2500, 10-5000, 10-10,000, 10-25,000, or 10-50,000 nucleotides. In certain embodiments, n is 0-15, 0-25, 0-50, 0-100, 0-150, 0-250, 0-500, 0-1000, 0-2500, 0-5000, 0-10,000, 0-25,000, or 0-50,000 amino acids.

In certain embodiments, A which comprises either $X_n$ or $X_nY[M]X_n$ is joined via a linker L with a N, comprising $x_nP1\text{-}U\text{---}P2x_n$.

In certain embodiments, A-L-N is:

$$X_{na}Y[M]X_{na}\text{-}L\text{-}x_{nn}P1\text{-}U\text{---}P2x_{nn},$$

wherein X is an amino acid; na is a number of amino acids; Y is a modified amino acid; M is a modification, wherein $X_{na}Y[M]X_{na}$ is least 5 amino acids; L is a linker; x is any nucleotide, nn is a number of nucleotides, P1 and P2 are primer sequences, and U is a unique nucleotide sequence. In certain embodiments, U is 10-50, 10-100, 10-250, 10-500, 10-1000, 10-2500, 10-5000, 10-10,000, 10-25,000, or 10-50,000 nucleotides. In certain embodiments, P1 and P2 each are independently 10-35, 10-40, 10-45, 10-50, 10-55, 10-60, 10-65, 10-70, 10-75, 10-100, 10-250, 10-500, or 10-1000 nucleotides. In certain embodiments, na is 0-15, 0-25, 0-50, 0-100, 0-150, 0-250, 0-500, 0-1000, 0-2500, 0-5000, 0-10,000, 0-25,000, or 0-50,000 amino acids. In certain embodiments, nn is 0-15, 0-25, 0-50, 0-100, 0-150, 0-250, 0-500, 0-1000, 0-2500, 0-5000, 0-10,000, 0-25,000, 0-50,000 or 0-100,000 nucleotides.

In certain embodiments, L is a chemical linker. In certain embodiments, the linker comprises two reactive terminal groups that can chemically interact with the two segments A and N. In certain embodiments, the linker L is 1-10 atoms, 1-25 atoms, 1-50 atoms, 1-100 atoms, 1-200 atoms, 1-500 atoms, 1-1000 atoms, 1-5000 atoms, 1-10,000 atoms, 1-50,000 atoms, or 1-100,000 atoms in length.

In certain aspects the invention provides sets of polypeptide-oligonucleotide conjugates described herein comprising at least two of the polypeptide-oligonucleotide conjugates of any of the preceding embodiments. In certain embodiments, the set comprises at least 5, at least 10, at least 15, at least 20, at least 25, at least 30, at least 35, at least 40, at least 50, at least 60, at least 70, at least 80, at least 90, at least 100, at least 125, at least 150, at least 175, or at least 200 of the polypeptide-oligonucleotide conjugates of any of the preceding embodiments.

In certain aspects the invention provides kits comprising the polypeptide-oligonucleotide conjugate described herein. In certain embodiments, the kits further contain one or more reagents necessary to perform a ChIP assay and/or one or more reagents necessary to perform chromatin fragment modification. In certain embodiments, the one or more kit reagents necessary to perform the ChIP assay are RNase A, Proteinase K, formaldehyde, glycine, PBS, cell lysis buffer, Triton X-100, protease inhibitor cocktails, wash buffer, elution buffer, or a ChIP antibody. In certain embodiments, the one or more kit reagents necessary to perform the chromatin fragment modification are Klenow DNA polymerase, DNA polymerase, T4 ligase, T4 polynucleotide kinase, T4 DNA polymerase, Klenow fragment 3' to 5' exo minus, enzyme reaction buffer, dATP, dNTPs, ultrapure water, TE, PCR or sequencing specific adapter, or a PCR or sequencing primer. In certain embodiments, the kits of any of the preceding embodiments, contain 1, 5, 10, 15, 20, 25, 30, 35, 40, 45, 50, 55, 60, 65, 70, 75, 80, 85, 90, 95, 100, 200, 300, 400, 500, 1000 different polypeptide-oligonucleotide conjugates of the formula A-L-N described herein.

In certain aspects the invention provides the use of a polypeptide-oligonucleotide conjugate described herein in an immunoprecipitation assay.

In certain aspects the invention provides a method of validating a chromatin immunoprecipitation (ChIP) assay result, wherein the method includes:
(a) obtaining an input sample of the genomic material of interest and of one or more of the polypeptide-oligonucleotide conjugates described herein,
(b) performing a ChIP assay, thereby processing, in parallel to the genomic material of interest of (a), the one or more polypeptide-oligonucleotide conjugates of (a),
(c) obtaining a processed sample of the polypeptide-oligonucleotide conjugate and the genomic material of interest processed in (b), and
(d) analyzing the samples obtained in (c), thereby obtaining a value and/or signal for each of the analyzed processed samples, and
(e) validating the ChIP assay result based on the value and/or signal obtained in (d).

In certain embodiments, the method includes a validation step that includes one or more comparisons of the value and/or signal of the input sample and the value and/or signal of the processed sample of C1 with the value and/or signal of the input sample and the value and/or signal of the processed sample of C2, wherein
(a) C1 is the genomic material of interest (e.g. immunoprecipitated nucleic acid, such as DNA) and C2 is a polypeptide-oligonucleotide conjugate, wherein C2 is a polypeptide-oligonucleotide conjugate immunoprecipitated with an antibody that is specific for the polypeptide-oligonucleotide conjugate (C2S), or C2 is a polypeptide-oligonucleotide conjugate immunoprecipitated with an antibody that is non-specific for the polypeptide-oligonucleotide conjugate (C2N), and/or
(b) C1 is a polypeptide-oligonucleotide conjugate immunoprecipitated with an antibody that is specific for the polypeptide-oligonucleotide conjugate and C2 is a polypeptide-oligonucleotide conjugate immunoprecipitated with an antibody that is non-specific for the polypeptide-oligonucleotide conjugate.

In certain embodiments, the methods described herein allow to conclude that when
(i) the value and/or signal of the processed sample in (a) of C1 and C2S is significantly higher than the value and/or signal of the input sample (e.g. non-iimunoprecipitated nucleic acid or cell extract, such as whole cell extract), then the genomic sample comprises an epitope specific for the antibody that is specific for C2S,
(ii) the value and/or signal of the processed sample in (a) of C1 and C2N is significantly higher than the value and/or signal of the input sample, then the genomic sample is non-specifically amplified or immunoprecipitated and the value or signal obtained is discarded,
(iii) the value and/or signal of the processed sample in (a) of C1 is not significantly higher than the value and/or signal of the input sample and the value and/or signal of the processed sample of C2S is significantly higher than the value and/or signal of the input sample, then the genomic sample does not comprise an epitope specific for the antibody that is specific for C2S,
(iv) the value and/or signal of the processed sample in (a) of C1 is significantly higher than the value and/or signal of the input sample and the value and/or signal of the processed sample of C2S is not significantly higher than the value and/or signal of the input sample, then the genomic sample is non-specifically amplified or immunoprecipitated and the value or signal obtained is discarded,
(v) the value and/or signal of the processed sample in (b) of C1 is significantly higher than the value and/or signal of the input sample and the value and/or signal of the processed sample of C2 is not significantly higher than the value and/or signal of the input sample, then the data obtained is analyzed,
(vi) the value and/or signal of the processed sample in (b) of C1 and C2 is significantly higher than the value and/or signal of the input sample, then the data obtained is not analyzed and is discarded.

In certain embodiments, the value and/or signal for the input sample and the processed sample are calculated as ratios.

In certain aspects the invention provides a method of screening an antibody for use in a chromatin immunoprecipitation (ChIP) assay, the method includes:
(a) contacting an antibody specific for an antigen of interest with one or more polypeptide-oligonucleotide conjugate, wherein at least one of the polypeptide-oligonucleotide conjugates comprises the antigen of interest and at least one polypeptide-oligonucleotide conjugate does not comprise the antigen of interest (b) performing a ChIP assay, thereby processing the oligonucleotide conjugate comprising the antigen of interest and the polypeptide-oligonucleotide conjugate not comprising the antigen of interest in parallel, (c) obtaining a processed sample of the polypeptide-oligonucleotide conjugate in (b), (d) analyzing the samples obtained in (c), thereby obtaining a value and/or signal for each the oligonucleotide conjugate comprising the antigen of interest and the polypeptide-oligonucleotide conjugate not comprising the antigen of interest, and (e) comparing the obtained values and/or signals, wherein when the value and/or signal obtained form the oligonucleotide conjugate comprising the antigen of interest is significantly higher than the value and/or signal obtained form the oligonucleotide conjugate not comprising the antigen of interest, then the antibody is useful in a ChIP assay. In certain embodiments, performing a ChIP assay in (b) comprises one or more steps of:

(a) immobilizing the antibody and specifically bound material, (b) reducing the amount of non-specifically bound material, (c) releasing the specifically bound material from the antibody, (d) fragmenting proteinaceous material, and/or (e) purifying nucleic acid material.

In certain aspects the invention provides a method of normalizing chromatin immunoprecipitation (ChIP) assay data, wherein the method includes:

(a) obtaining an input sample of the genomic material of interest and of one or more of the polypeptide-oligonucleotide conjugates, (b) performing a ChIP assay, thereby processing, in parallel to the genomic material of interest in (a), the one or more polypeptide-oligonucleotide conjugates of (a), (c) obtaining a processed sample of the polypeptide-oligonucleotide conjugate and the genomic material of interest processed in (b), (d) analyzing the samples obtained in (c), thereby obtaining a value and/or signal for each of the analyzed processed samples, and (e) normalizing the values and/or signals obtained in (d) for each of the processed samples using the values obtained in (d) for each of the input samples. In certain embodiments, parallel processing in (b) includes contacting the genomic material with the one or more polypeptide-oligonucleotide conjugates. In certain embodiments, the contacting of the genomic material with the one or more polypeptide-oligonucleotide conjugates is performed after fragmentation of the genomic material and before the resulting sample is contacted with an antibody.

In certain embodiments, performing a ChIP assay in (b) comprises one or more steps of:

(a) fragmenting genomic material of interest, (b) contacting the fragmented genomic material and the one or more polypeptide-oligonucleotide conjugates with an antibody, (c) immobilizing the antibody and specifically bound material, (d) reducing the amount of non-specifically bound material, (e) releasing the specifically bound material from the antibody, (f) reversing a previous cross-linking reaction, (g) fragmenting proteinaceous material, and/or (h) purifying nucleic acid material.

In certain embodiments, analyzing the processed sample in (d) comprises performing a polymerase-chain reaction, a sequencing reaction, and/or a hybridization reaction. In certain embodiments, normalizing in (e) comprises calculating ratios for input sample and processed sample for the genomic material and the one or more polypeptide-oligonucleotide conjugates.

Other aspects of the invention relate to control agents for immunoprecipitation (IP) assays, including but not limited to RNA-IP followed by sequencing (RIP-seq), methylated-DNA IP followed by sequencing (mDIP-seq), bisulphite sequencing (BS-seq), High-throughput sequencing of RNA isolated by crosslinking IP (HITS-CLIP), formaldehyde-assisted isolation of regulatory elements followed by sequencing (FAIRE-seq), and micrococcal nuclease digestion followed by sequencing (MNase-seq). Control agents provided herein comprise the formula:

X—B or B—X, where X is a molecule (e.g., polypeptide, such as A described above, or a polynucleotide), and B (also referred to as "barcode") is an oligonucleotide (e.g., DNA or RNA) comprising, for example, 10 nucleotides, wherein the sequence of nucleotides of B uniquely identifies X. In some configurations, a linker L is used to conjugate B and X. Examples of control agents include, but are not limited to, barcoded DNA-peptide conjugates, barcoded RNA-peptide conjugates, barcoded methylated DNA oligos, and assembled nucleosomes conjugated to barcoded DNA.

Additional aspects and embodiments of the invention are described in international application number PCT/US2011/054072, filed Sep. 29, 2011, which claims the benefit under 35 U.S.C. §119(e) of U.S. provisional application Ser. No. 61/387,689, filed Sep. 29, 2010, each of which is incorporated by reference herein in its entirety.

This application refers to various issued patents, published patent applications, journal articles, and other publications, all of which are incorporated herein by reference for the purposes cited herein.

BRIEF DESCRIPTION OF THE FIGURES

FIGS. 2-1 and 2-2 are schematics depicting some common posttranslational modifications of histones and the names of the enzymes thought to be responsible for the modification. Globular domains of each core histone are represented as ovals.

DEFINITIONS

Figure 1:
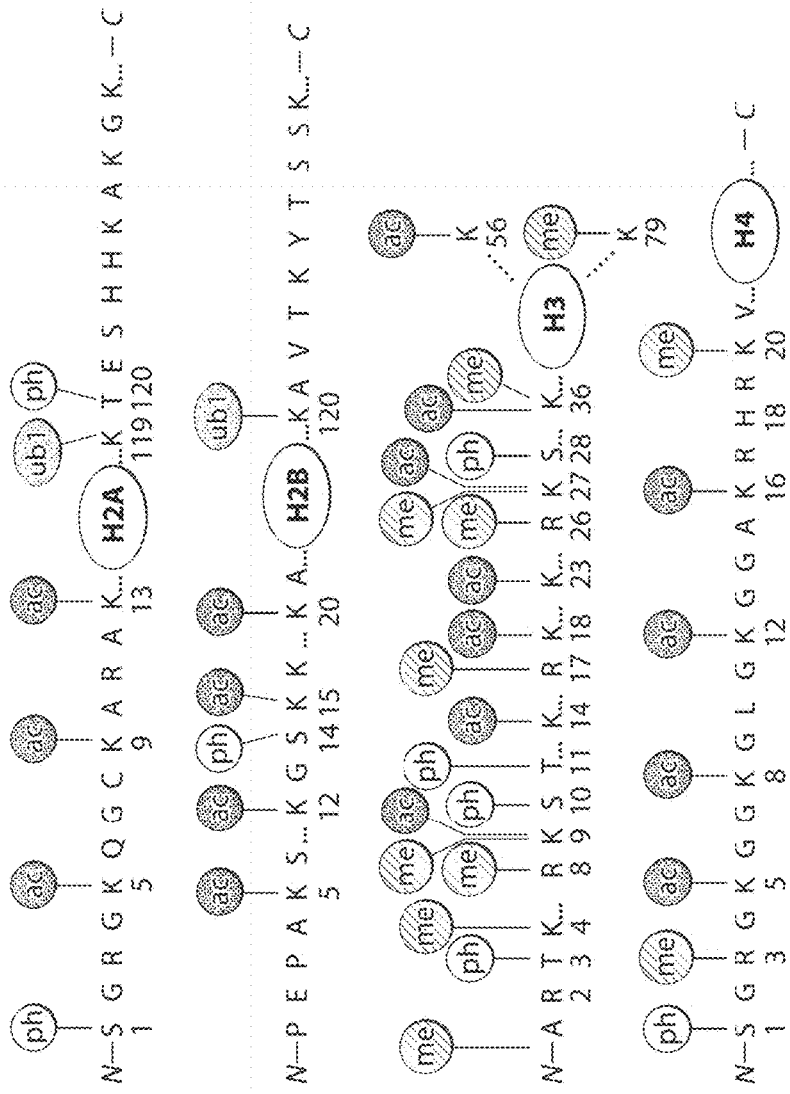
FIG. 1 is a schematic depicting some common posttranslational modifications of human nucleosomal histones. The modifications include acetylation (ac), methylation (me), phosphorylation (ph) and ubiquitination (ubl). Globular domains of each core histone are represented as ovals.

"Amino acids" may be referred to herein by either their commonly known three letter symbols or by the one-letter symbols recommended by the IUPAC-IUB Biochemical Nomenclature Commission. Amino acid residues in proteins or peptides are abbreviated as follows: phenylalanine is Phe or F; leucine is Leu or L; isoleucine is Ile or I; methionine is Met or M; valine is Val or V; serine is Ser or S; proline is Pro or P; threonine is Thr or T; alanine is Ala or A; tyrosine is Tyr or Y; histidine is His or H; glutamine is Gln or Q; asparagine is Asn or N; lysine is Lys or K; aspartic acid is Asp or D; glutamic Acid is Glu or E; cysteine is Cys or C; tryptophan is Trp or W; arginine is Arg or R; and glycine is Gly or G. For further description of amino acids, see *Proteins: Structure and Molecular Properties* by Creighton T. E. (1983), W. H. Freeman & Co., New York, incorporated herein by reference.

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

A "non-natural amino acid" refers to an amino acid that is not one of the 20 common amino acids, pyrrolysine or selenocysteine; The term "non-natural amino acid" includes, but is not limited to, amino acids that occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs/orthologs, and alleles of the agents described herein.

Conservative amino acid substitutions are amino acid substitution in which the substituted amino acid residue is of similar charge as the replaced residue and/or is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T, and C; (c) the amido amino acids, Q and N; (d) the aromatic amino acids, F, Y, and W; (e) the basic amino acids, K, R, and H; and (f) the acidic amino acids, E and D. Substitutions which are charge neutral and which replace a residue with a smaller residue may also be considered conservative substitutions even if the residues are in different groups (e.g., replacement of phenylalanine with the smaller isoleucine). Methods for making amino acid substitutions, additions, or deletions are well known in the art, e.g., polymerase chain reaction (PCR)-directed methods (*Molecular Biology: Current Innovations and Future Trends*. by Griffin A. M. and Griffin H. G. (1995) Horizon Scientific Press, Norfolk, U.K; *Modern Genetic Analysis*. by Griffith A. J., Second Edition, (2002) H. Freeman and Company, New York, N.Y.).

An "antigen" as used herein may be any amino acid fragment (modified or unmodified) of 5 amino acids or more which are recognized by an antibody or for which recognizing antibodies can be raised. In certain embodiments, antigens may comprise modifications of an amino acid, such as acetylation, methylation (e.g. mono-, di-, tri-), phosphorylation, ubiquitination e.g. mono-, di-, tri-, poly-), sumoylation, ADP-ribosylation, citullination, biotinylation, and cis-trans isomerization. In other embodiments, antigens may comprise specific mutations, such as point mutations. In other yet embodiments, antigens may comprise wild-type amino acid sequence.

A "bifunctional linker" refers to a polymer comprising two discrete functional groups that are capable of reacting specifically with other moieties (including but not limited to, $NH_2$—, $SH$—, —$COOH$, —$CO$, and —$C_nH_n$ groups) to form covalent or non-covalent linkages. Many procedures and linker molecules for attachment of various compounds to peptides are known. e.g. U.S. Pat. Nos. 4,671,958; 4,659,839; 4,680,338; and 4,569,789. A bi-functional linker or multi-functional linker may be any desired length or molecular weight, and may be selected to provide a particular desired spacing or conformation between one or more molecules linked to the polypeptide.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. As used herein, the terms encompass amino acid chains of any length, including full length proteins, wherein the amino acid residues are linked by covalent peptide and/or pseudopeptide bonds.

The term "post-translational modification" refers to any modification of a natural or non-natural amino acid that occurs or would occur to such an amino acid after it has been incorporated into a polypeptide chain in vivo or in vitro. Such modifications include, but are not limited to, acetylation, methylation (e.g. mono-, di-, tri-), phosphorylation, ubiquitination (e.g. mono-, di-, tri-, poly-), sumoylation, ADP-ribosylation, citullination, biotinylation, and cis-trans isomerization. Such modifications may be introduced synthetically, e.g. chemically, during polypeptide synthesis or enzymatically after polypeptide synthesis or polypeptide purification.

By "screen" or "screening" is meant to test a compound (e.g. an antibody) with a particular characteristic or desired property. Testing may be conducted in vivo or in vitro, for example in a biochemical assay, such as those described herein. These characteristics or desired properties of the compound (e.g. antibody) may be chemical, biological, or physical in nature or a combination thereof. Desired characteristics or desired properties of antibodies in ChIP may, for example, be high affinity and/or high specificity for a particular antigen of interest.

DETAILED DESCRIPTION OF CERTAIN EMBODIMENTS OF THE INVENTION

Controls for immunoprecipitation assays, e.g., ChIP assays, that are currently used have several major drawbacks with regard to their specificity and their ability to distinguish between true and false negative or positive results obtained by the procedure. For example, a positive antibody control for the ChIP technique that is commonly used is Histone H3 (tri methyl K4) when analyzing active genes. As a negative control, use of an antibody that recognizes a non-chromatin epitope, such as an anti-GFP antibody, is common. Such control antibodies however, do not validate the ChIP procedure (i.e. are not positive and negative controls for the success of the ChIP experiment) per se. For example, if Histone H3 tri methyl K4 is absent at the particular genomic locus of interest, then even a highly efficient and specific ChIP antibody will not immuno-precipitate chromatin from this region and thus will not be an appropriate positive control. An anti-GFP antibody will not provide a good negative control for non-specific binding of antibodies directed to histone modifications. Further, chromatin remodeling may move or remove histones at a particular locus e.g. an active promoter, so use of a control antibody against a non-modified histone, such as Histone H3, may be necessary to confirm the preservation of nucleosomes at particular genomic loci. If a ChIP signal is weak or non-existent, troubleshooting may include use of different antibody, optimizing of the cross-linkage time course, the fragmentation, binding, wash, and/or elution conditions. Current ChIP protocols recommend using purified histone H3 and H1 as positive controls for the quality of the experimental histone preparation, when analyzing histone modifications.

Existing technologies for ChIP antibody validation and ChIP quality controls, e.g. using primer and probe sets specific for particular genes or chromatin regions. For example, probes and primers may be provided for certain housekeeping gene loci, tissue-specific gene loci, heterochromatic loci or gamma actin loci (Abcam, Cambridge Mass.). These control kits can be limiting in that the source material can only be detected by the primer/probe pairs in a species-specific manner (e.g. to human genes, such as hsGAPDH, hsMyoD, hsSATa, and hsAct1) and in that the histone modification, for which a control is necessary, needs to be determined prior to conducting the ChIP assay. For example, hsGAPDH primer/probe sets may provide a positive control for a specific histone modification associated with active gene transcription, such as Histone H3 K9 acetylation, and may provide a negative control for a specific histone modification associated with silencing, such as Histone H3 K9 tri methylation. hsMyoD primer/probe sets may provide a positive control for a specific histone modification associated with gene silencing, such as Histone H3 K27 dimethylation, and may provide a negative control for a specific histone modification associated with active gene transcription, such as Histone H3 K9 acetylation. hsSATa primer/probe sets may provide a positive control for a specific histone modification associated with heterochromatin, such as Histone H3 K9 trimethylation, and may provide a negative control for a specific histone modifications associated with active gene transcription, such as Histone H3 K4 trimethylation.

These controls are based on empirically acquired knowledge of specific gene regions and since biological systems are dynamic, these controls can vary, for example, between cell types or between the same cells exposed to different conditions. These controls are not available for all of the known histone modifications. Moreover, it is very difficult to obtain and/or use such controls for assays that analyze non-histone proteins, such as DNA-binding proteins (chromatin-associated factors, e.g. transcription factors, activator/repressor complex constituents, DNA replication or DNA repair factors, etc.) and non-histone modifications, such as, for example, post-translational modifications of transcription factors.

Further, as it is difficult to combine these controls in cases involving several modifications that are probed in a ChIP assay these control experiments would need to be conducted sequentially, requiring more sample and more hands-on time.

*Polypeptide-Oligonucleotide Conjugates as Controls for IP Assays*—e.g., ChIP:

It would be a distinct advantage to be able to monitor the steps of an ChIP protocol and its efficiency using just one set of antibodies, for example those that are directed to the histone modification of interest, and to have specific control agents that can undergo all the process steps required for ChIP in parallel to the genomic material. Pre-determined amounts of such control could, for example, be added to the assay at the beginning of the immunoprecipitation procedure (e.g. at the step when fragmented chromatin is contacted with the ChIP antibody). Further it would be useful to provide a pool of controls for several histone modifications that can be processed in parallel without the need to determine the control prior to performing the ChIP assay.

Provided herein are IP assays (e.g., ChIP assays) control agents that are i) specific for an antigen of interest (e.g. a post-translational histone modification or non-histone protein modification and corresponding unmodified sequences) and ii) can be pooled. In certain embodiments, the ChIP assays control agents may be provided as part of a kit, for example a kit that comprises one or more additional reagents necessary to perform ChIP assays and or nucleic acid sequence analysis.

Provided herein are polypeptide-oligonucleotide conjugates of the general formula:

A-L-N, wherein "A" is a polypeptide of at least 5 amino acids, "L" is a linker, and "N" is an oligonucleotide of at least 10 bases as ChIP assays control agents.

"A" as used herein consists of at least 5 amino acids. In certain embodiments, A is 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 amino acids. In certain embodiments, A is 151 or more amino acids. In certain embodiments, A is 5-15, 5-25, 5-50, 5-100, 5-250, 5-500, 5-1000, 5-2500, 5-5000, 5-10,000, 5-25,000, 5-50,000 or 5-100,000 amino acids.

In certain embodiments, A comprises 1, 2, 3, 4, 5, 6, 7, 8, 9, 10, 11, 12, 13, 14, 15, 16, 18, 19, 20 or more amino acids at least in part derived from a histone protein, such as, for example, histone H2A, H2B, H3, or H4. In certain embodiments, A comprises 5-15, 5-25, 5-50, 5-100, 5-250, 5-500, 5-1000, 5-2500, 5-5000, 5-10,000, 5-25,000, or 5-50,000 amino acids at least in part derived from a histone protein, such as histone H2A, H2B, H3, or H4. In certain embodiments, A comprises 1, 2, 3, 4, 5, 6, 7, 8, 9, 10, 11, 12, 13, 14, 15, 16, 18, 19, 20 or more (up to the total amino acid sequence of the histone) amino acids derived from the N-terminus of a histone protein, such as the N-terminus of histone H2A, H2B, H3, or H4. In other embodiments, A comprises 1, 2, 3, 4, 5, 6, 7, 8, 9, 10, 11, 12, 13, 14, 15, 16, 18, 19, 20 or more (up to the total amino acid sequence of the histone) amino acids derived from the C-terminus of a histone protein, such as the C-terminus of histone H2A, H2B, H3, or H4. In certain embodiments, A comprises an amino acid sequence of 1, 2, 3, 4, 5, 6, 7, 8, 9, 10, 11, 12, 13, 14, 15, 16, 18, 19, 20 or more (up to 36) amino acids of the following sequences:

H2A N-terminus: SGRGKQGCKARAK (SEQ ID NO: 1)
H2A C-terminus: VLLPKKTESHHKAKGK (SEQ ID NO: 2)
H2B N-terminus: PEPAKSAPAPKKGSKKAVTK (SEQ ID NO: 3)
H2B C-terminus: AVSEGTKAVTKYTSSK (SEQ ID NO: 4)
H3 N-terminus: ARTKQTARKSTGGKAPRKQLATKAARKSAPATGGVK (SEQ ID NO: 5)
H3 globular domain: QRLVREIAQDFKTDLRFQSSAVMALQEA (SEQ ID NO: 6)
H4 N-terminus: SGRGKGGKGLGKGGAKRHRKVLRDNIQGITKPAIRRLA (SEQ ID NO: 7)

In certain embodiments, A comprises an amino acid sequence of 1, 2, 3, 4, 5, 6, 7, 8, 9, 10, 11, 12, 13, 14, 15, 16, 18, 19, 20 or more (up to 36) amino acids of SEQ ID NOs: 1-7, wherein one or more of the amino acids is modified. In certain embodiments, the one or more modification is an acetylation, a methylation (e.g. mono-, di-, tri-), a phosphorylation, or an ubiquitination (e.g. mono-, di-, tri-, poly-), sumoylation, ADP-ribosylation, citullination, biotinylation, or cis-trans isomerization.

In certain embodiments, A comprises:

$X_n Y[M]X_n$, wherein X is an amino acid, n is a number of amino acids, Y is a modified amino acid, M is a modification. "n" in certain embodiments, is 0-15, 0-25, 0-50, 0-100, 0-150, 0-250, 0-500, 0-1000, 0-2500, 0-5000, 0-10,000, 0-25,000, or 0-50,000 amino acids.

Non-limiting examples of A comprising either no modifications or one or more modifications are:

1) Non-limiting examples for A derived from H2A are:

$X_n S[ph]GRGX_n$, (SEQ ID NO: 8)

$X_n GRGK[ac]QGCX_n$, (SEQ ID NO: 9)

$X_n S[ph]GRGKQGCX_n$, (SEQ ID NO: 10)

$X_n SGRGK[ac]QGCX_n$, (SEQ ID NO: 11)

$X_n QGCK[ac]ARAX_n$, (SEQ ID NO: 12)

$X_n K[ub]TESX_n$, (SEQ ID NO: 13)

$X_n KT[ph]ESHX_n$, (SEQ ID NO: 14)

$X_n K[ub]TESHX_n$, (SEQ ID NO: 15)

$X_n KT[ph]ESHX_n$, (SEQ ID NO: 16)

$X_n SGRGKQGCKARAKX_n$, (SEQ ID NO: 17)

$X_n VLLPKKTESHHKAKGKX_n$, (SEQ ID NO: 18)

2) Non-limiting examples for A derived from H2B are:

$X_n PEPAK[ac]SX_n$, (SEQ ID NO: 19)

$X_n K[ac]GSKKX_n$, (SEQ ID NO: 20)

$X_n KGS[ph]KKX_n$, (SEQ ID NO: 21)

$X_n KGSK[ac]KX_n$, (SEQ ID NO: 22)

$X_n K[ub]AVTKYTSSX_n$, (SEQ ID NO: 23)

$X_n PAPKK[ac]GSKKAX_n$, (SEQ ID NO: 24)

$X_n PAPKKGSK[ac]KAVTKX_n$,, (SEQ ID NO: 25)

$X_n KGS[ph]KKX_n$, (SEQ ID NO: 26)

$X_n PEPAKSAPAPKKGSKKAVTKX_n$ (SEQ ID NO: 27)

$X_n AVSEGTKAVTKYTSSKX_n$ (SEQ ID NO: 28)

3) Non-limiting examples for A derived from H3 are:

$X_n ARTKQTARKSTGGKAPRKQLATKAARKSAPATGGVKX_n$, (SEQ ID NO: 29)

$X_n AR[me]TKX_n$, (SEQ ID NO: 30)

$X_n RT[ph]KX_n$, (SEQ ID NO: 31)

$X_n ARTK[me]QTAX_n$, (SEQ ID NO: 32)

$X_n ARKS[ph]TGGK[ac]APRX_n$ (SEQ ID NO: 34)

$X_n ARTKQTAR[me]KSTGGKAX_n$, (SEQ ID NO: 35)

$X_n RKST[ph]GGK[ac]AP_n$, (SEQ ID NO: 36)

$X_n ARTKQTARKSTGGKAPRKQLATKAAR[me]KSAPATGGVKX_n$, (SEQ ID NO: 37)

$X_n R[me]KSAX_n$, (SEQ ID NO: 38)

-continued

X$_n$ARK[me]SAPX$_n$, (SEQ ID NO: 39)

X$_n$RK[ac]SAX$_n$, (SEQ ID NO: 40)

X$_n$S[ph]APAX$_n$, (SEQ ID NO: 41)

X$_n$QRLVREIAQDFKTDLRFQSSAVMALQEAX$_n$ (SEQ ID NO: 42)

X$_n$DFK[me]TDX$_n$ (SEQ ID NO: 43)

X$_n$K[me]TDLRFQSSX$_n$ (SEQ ID NO: 44)

X$_n$ARTKQTARKS[ph]TGGKAPRKQLATKAARKS[ph]APATGGVKX$_n$ (SEQ ID NO: 45)

X$_n$ARKS[ph]TGGK[ac]APRX$_n$ (SEQ ID NO: 46)

X$_n$RTK[me]QTARK[me]STX$_n$ (SEQ ID NO: 47)

X$_n$TK[me]QTARK[me]STGGKAPRKQLATKAARK[me]SAPATX$_n$ (SEQ ID NO: 48)

4) Non-limiting examples for A derived from H4 are:

X$_n$S[ph]GRX$_n$ (SEQ ID NO: 49)

X$_n$SGR[me]GKGGKGLGKGGAKRHRKVLRDNIQGITKPAIRRLAX$_n$ (SEQ ID NO: 50)

X$_n$SGRGK[ac]GGKX$_n$ (SEQ ID NO: 51)

X$_n$SGRGKGGK[ac]GLGKGGAKRHRKVLRX$_n$ (SEQ ID NO: 52)

X$_n$GKGGKGLGK[ac]GGAKRX$_n$ (SEQ ID NO: 53)

X$_n$GKGGAK[ac]RHRKVLRDNIQGITKX$_n$ (SEQ ID NO: 54)

X$_n$K[me]VLX$_n$ (SEQ ID NO: 55)

X$_n$KGLGKGGAKRHRK[me]VLRDNIQGITKX$_n$ (SEQ ID NO: 56)

X$_n$SGRGKGGKGLGKGGAKRHRKVLRDNIQGITKPAIRRLAX$_n$ (SEQ ID NO: 57)

X$_n$GRGK[ac]GGKGLGK[ac]GGAKRHX$_n$ (SEQ ID NO: 58)

Figures 1, 2:
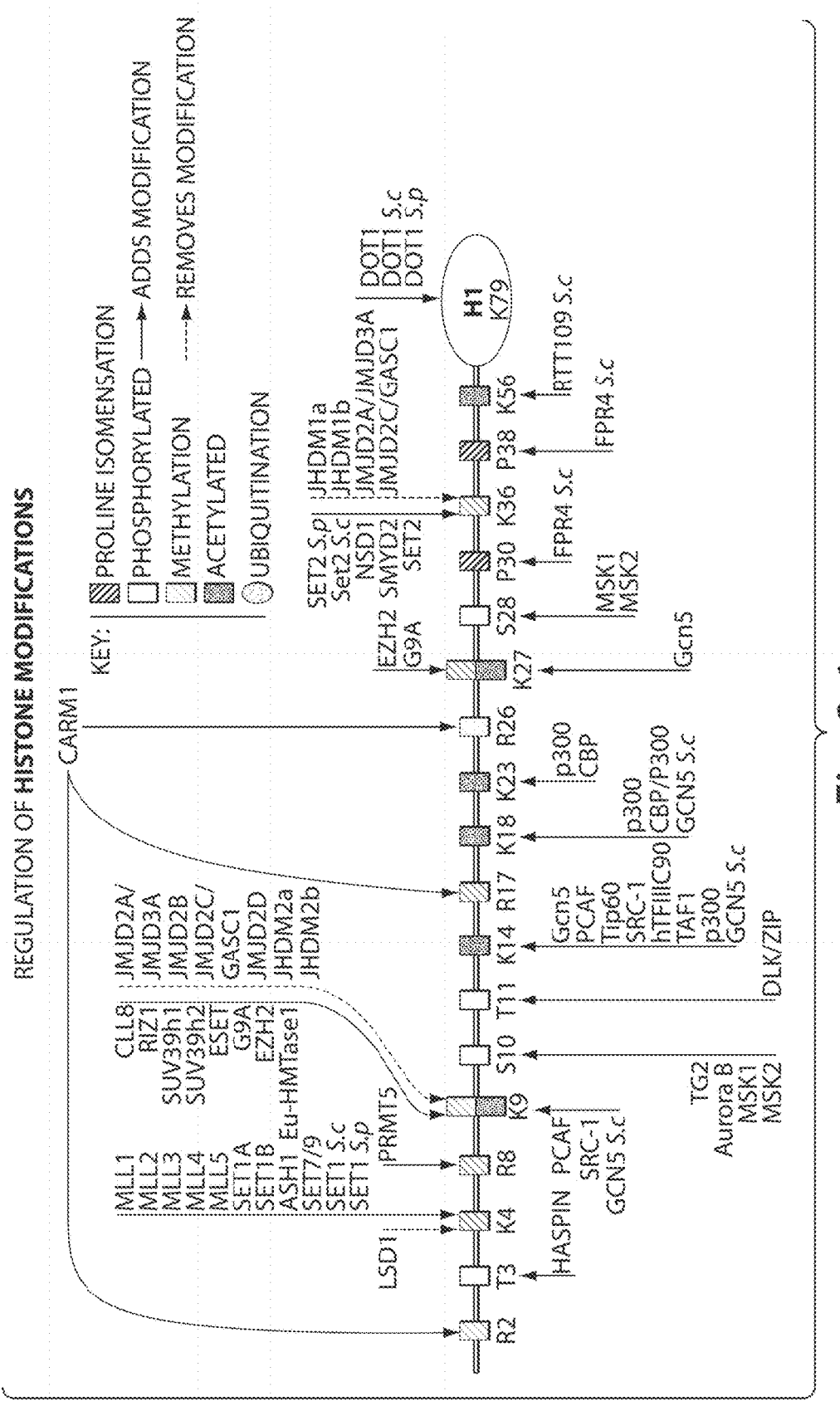
Figure 2:
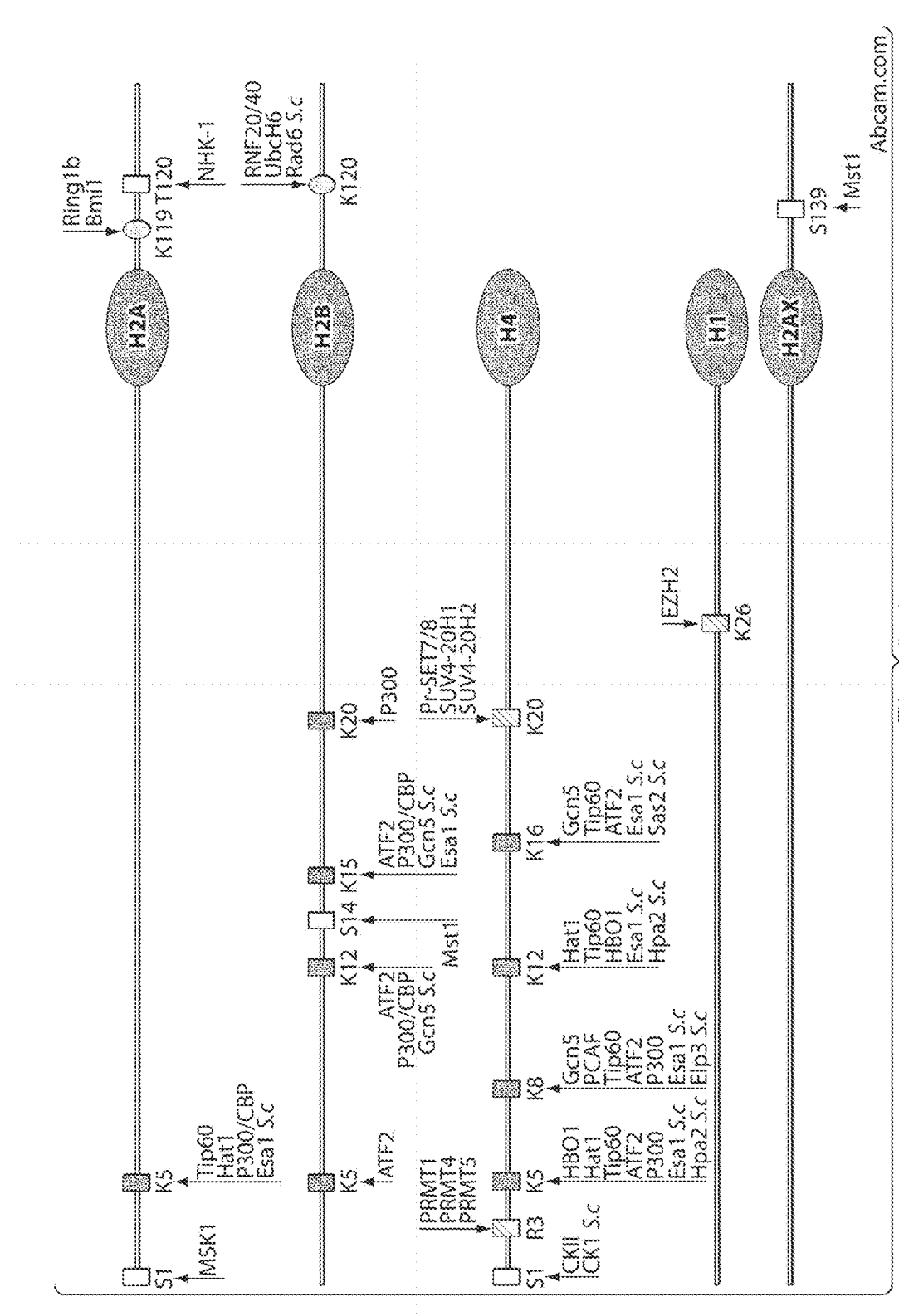
Figure 3A:
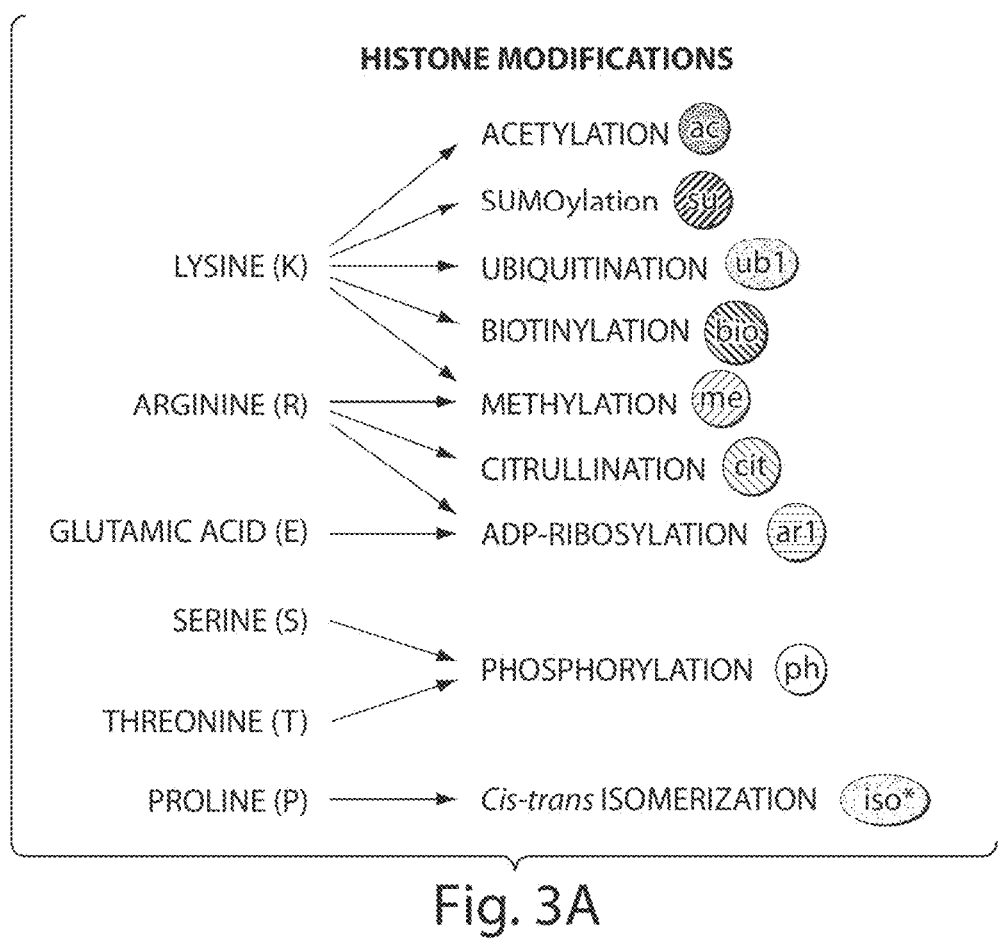
FIG. 3A is a schematic depicting various modifications that may occur at specific amino acid residues.
Figure 3B:
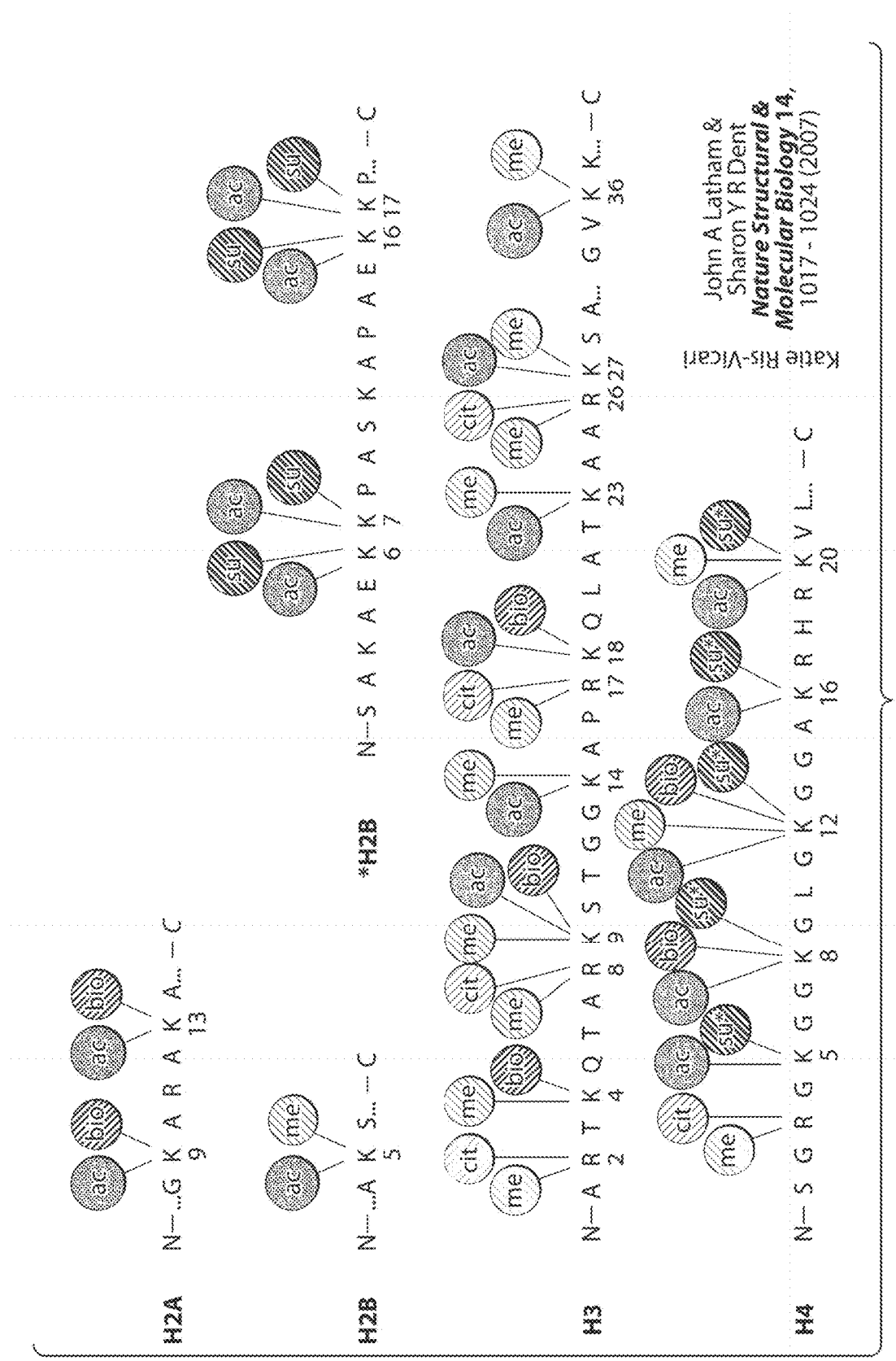
FIG. 3B is a schematic depicting the modifications listed in FIG. 3A at their location on the histones.

X$_n$GGK[ac]GLGKGGAK[ac]RHX$_n$, (SEQ ID NO: 59)

wherein [ac] is acetylation, [ph] is phosphorylation, [ub] is ubiquitination, [me] is mono-, di- or tri-methylation, "X" is any amino acid and "n" is a number of amino acids. "n" in certain embodiments, is 0-15, 0-25, 0-50, 0-100, 0-150, 0-250, 0-500, 0-1000, 0-2500, 0-5000, 0-10,000, 0-25,000, or 0-50,000 amino acids. Other modifications are known in the art and are depicted for example in FIGS. 1, 2, and 3. The examples given here are for illustrative purposes only and are not meant to be limiting in any way. One of ordinary skill would know how to modify the examples given here for A, for example, the number of amino acids derived from the wild-type sequence of histones H2A, H2B, H3, and H4 exemplified here may be reduced or additional wild-type sequence may be added (N- and/or C-terminal of the exemplified sequence), one or more amino acids may be changed, e.g. using a conservative amino acid exchange or a non-conservative amino acid exchange (for example species-specific exchanges to generate homologs/orthologs), one or more non-natural amino acids may replace the amino acids exemplified, pseudopeptide units may be inserted, additional combinations of modifications e.g. acetylation, phosphorylation, ubiquitination, mono-, di- or tri-methylation, sumoylation, ADP-ribosylation, citullination, biotinylation, and cis-trans isomerization may be generated. Such modifications are well within the skills of an ordinary artisan (and depicted in FIGS. 3A and 3B), any desired A segments may be generated and all such A segments are contemplated herein. For example, lysine (K) may be acetylated, sumoylated, ubiquitinated, biotinylated, or methylated; arginine (R) may be methylated, citullinated or ADP-ribosylated; glutamic acid (E) may be ADP-ribosylated; serine (S) and threonine (T) may be phosphorylated, and proline may be cis-trans-isomerated as depicted in FIGS. 3A and 3B. Such modifications may be specific to certain histones or all histones. Modifications may also be specific to certain species, such as mammals (human, mouse, rat, hamster, dog, cat, monkey, horse, sheep, cow), fish (e.g. zebrafish), yeast (e.g. *Saccharomyces cerevisiae, Schizosaccharomyces pombe, Candida albicans*), plant (e.g. *Arabidopsis thaliana, Nicotiana tabacum*, corn, algae), fruit fly (e.g. *Drosophila melanogaster*), nematodes (*Caenorhabditis elegans*) and others.

Further, additional A segments may be generated that comprise wild-type sequence of other histones, such as Histone H1 and H2AX. Histone H1, for example comprises a modification at lysine 26 (K26[me]) and histone H2AX comprises a modification at serine 139 (S139[ph]).

A segments for any known histone modification may be generated, including, but not limited to:

1) Modifications for Histone H1, for example H1 (phospho S1+T3), H1 (phospho S35), H1 (acetyl K63);

2) Modifications for Histone H2A, for example H2A (asymmetric di methyl R3), H2A (symmetric di methyl R3), H2A (acetyl K5), H2A (mono methyl R17), H2A (symmetric di methyl R77), H2A (Hydroxy P26), H2A (mono methyl K125), H2A (tri methyl K125), H2A (mono methyl K127), H2A (tri methyl K127), H2A (phospho S129);

3) Modifications for Histone H2B, for example H2B (acetyl K5), H2B (di methyl K5), H2B (Hydroxy P10), H2B (di methyl K43);

4) Modifications for Histone H3, for example H3 (mono methyl R2), H3 (citrulline 2+8+17), H3 (mono methyl K4), H3 (di methyl K4), H3 (tri methyl K4), H3 (di+tri methyl K4), H3 (acetyl K9), H3 (acetyl K9, phospho S10), H3 (mono methyl K9), H3 (di methyl K9), H3 (tri methyl K9), H3 (phospho S10), H3 (asymmetric di methyl R17), H3 (acetyl K18), H3 (acetyl K27), H3 (di methyl K27), H3 (tri methyl K27), H3 (mono methyl K27, tri methyl K27+K4), H3 (mono methyl K36), H3 (tri methyl K36), H3 (Hydroxy P38), H3 (mono methyl K79), H3 (di methyl K79), H3 (tri methyl K79), H3 (mono+di+tri methyl K79), H3 (Hydroxy P121), H3 (tri methyl K122);

5) Modifications for Histone H4, for example H4 (symmetric di methyl R3), H4 (acetyl K8), H4 (acetyl K12), H4 (mono methyl K20), H4 (tri methyl K20), H4 (phospho T30), H4 (Hydroxy P32), H4 (tri methyl K59), H4 (phospho T80), H4 (acetyl K91), H4 (phospho T96).

"N" as used herein consists of at least 10 nucleotides. In certain embodiments, N is 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 nucleotides. In certain embodiments, N is 10-25, 10-50, 10-100, 10-250, 10-500, 10-1000, 10-2500, 10-5000, 10-10,000, 10-25,000, 10-50,000 or 10-100,000 nucleotides.

In certain embodiments, N comprises a nucleotide sequence that is unique for a certain species (e.g. mammal, fish, yeast, plant, etc.) and/or produces a product that when amplified (e.g. by PCR) is unique to the species. In certain embodiments, the unique nucleotide sequence of N may not hybridize to a genomic fragment derived from the species. In certain embodiments, primers amplifying a unique portion of N will not amplify a fragment of genomic DNA derived from the species. In certain embodiments, primers amplifying a unique portion of N will not efficiently amplify a fragment of genomic DNA derived from the species, such as, that the size of the amplified genomic fragment may be much larger than the size of the portion amplified in N.

In certain embodiments, the nucleotide sequence of N is unique to the amino acid sequence and/or amino acid modification of A, such that each different nucleotide sequence (N) in a set of nucleotide sequences (N1, N2, N3, N4, N5, . . . ) uniquely identifies a different amino acid sequence and/or amino acid modification (A) in a set of such amino acid sequences and/or amino acid modifications (A1, A2, A3, A4, A5, . . . ). For example, if A1 is $X_nY[M_1]X_n$, wherein X is an amino acid, n is a number of amino acids, Y is a modified amino acid, $M_1$ is a modification, and A2 is $X_nY[M_2]X_n$, wherein $M_2$ is a different modification form $M_1$, then N1 comprises a nucleotide sequence that is unique to A1 and N2 comprises a nucleotide sequence that is unique to A2. "n" in certain embodiments, is 0-15, 0-25, 0-50, 0-100, 0-150, 0-250, 0-500, 0-1000, 0-2500, 0-5000, 0-10, 000, 0-25,000, or 0-50,000 amino acids. A unique sequence U may for example have a size from 10 nucleotides to 500 nucleotides, from 20 to 400, from 30 to 300, from 40 to 200, from 15 to 150, from 50 to 100, from 25 to 75, 45 to 65, or may be around 20, around 30, around 40, around 50, around 60, around 70, around 80, around 90, or around 100 nucleotides. In certain embodiments, U has a size from 10-1000, 10-2500, 10-5000, 10-10,000, 10-25,000, or 10-50,000 nucleotides. A unique sequence may differ from any other unique sequence by 1, 2, 3, 4, 5, 6, 7, 8, 9, 10, 11, 12, 13, 14, 15, 16, 18, 19, 20 or more nucleotides. In certain embodiments, the unique sequence differs from any other unique sequence by 25, 50, 75, 100, 250, 500, 1000, 2500, 5000, 10,000, 20,000 or more nucleotides.

In certain embodiments, N comprises:

$x_nP1-U—P2x_n,$ wherein x is any nucleotide, n is a number of nucleotides, P1 and P2 are primer sequences, and U is a unique sequence. In certain embodiments, the primer sequences can be between 10 and 35 nucleotides long, e.g. 10, 11, 12, 13, 14, 15, 16, 17, 18, 19, 20, 21, 22, 23, 24, 25, 26, 27, 28, 29, 30, 31, 32, 33, 34, or 35 nucleotides. In certain embodiments, the primer sequences can be 10-40, 10-45, 10-50, 10-55, 10-60, 10-65, 10-70, 10-75, 10-100, 10-250, 10-500, or 10-1000 nucleotides long. "n" in certain embodiments, is 0-15, 0-25, 0-50, 0-100, 0-150, 0-250, 0-500, 0-1000, 0-2500, 0-5000, 0-10,000, 0-25,000, 0-50,000 or 0-100,000 nucleotides.

In certain embodiments, a specific A, comprising either $X_n$ or $X_nY[M]X_n$, is joined via a linker L with a specific N, comprising $x_nP1-U—P2x_n$. In certain embodiments, wherein U is unique, P1 and P2 are the same for every specific A.

For example, the following A segments may be joined via L with the following N segments of A-L-N:

$X_{na}Y_1[M_1]X_{na}$-L-$x_{nn}P1$-$U_1$-$P2x_{nn}$ $X_{na}Y_2[M_2]X_{na}$-L-$x_{nn}P1$-$U_2$-$P2x_{nn}$ $X_{na}Y_2[M_2]X_{na}$-L-$x_{nn}P1$-$U_3$-$P2x_{nn}$ wherein "X" is an amino acid; "na" is a number of amino acids; $Y_1$, $Y_2$, $Y_3$ are different modified amino acids; $M_1$, $M_2$, $M_3$ are different modifications, wherein $X_{na}Y_1[M_1]X_{na}$ is least 5 amino acids; "L" is a linker; "x" is any nucleotide, "nn" is a number of nucleotides, P1 and P2 are primer sequences, and $U_1$, $U_2$, $U_3$ are unique nucleotide sequences. In certain embodiments, the primer sequences P1 and P2 are independently 10-35, 10-40, 10-45, 10-50, 10-55, 10-60, 10-65, 10-70, 10-75, 10-100, 10-250, 10-500, or 10-1000 nucleotides long. "na" in certain embodiments, is 0-15, 0-25, 0-50, 0-100, 0-150, 0-250, 0-500, 0-1000, 0-2500, 0-5000, 0-10,000, 0-25,000, or 0-50,000 amino acids. "nn" in certain embodiments, is 0-15, 0-25, 0-50, 0-100, 0-150, 0-250, 0-500, 0-1000, 0-2500, 0-5000, 0-10,000, 0-25,000, 0-50, 000 or 0-100,000 nucleotides. In certain embodiments, U has a size from 10-25, 10-50, 10-100, 10-250, 10-500, 10-1000, 10-2500, 10-5000, or 10-10,000 nucleotides.

As will be apparent to one of skill in the art, by using the same primer pair (P1 and P2), N comprising the three unique sequences $U_1$, $U_2$, $U_3$ can be sequenced. In this example, every specific U in N is linked to a specific A, comprising a modified amino acid.

It should be appreciated that an amplification sequence, e.g. P1 and/or P2, is not always needed and/or not always desired. In certain embodiments, N comprises:

$$x_n U x_n,$$

wherein x is any nucleotide, n is a number of nucleotides and U is a unique sequence. "n" in certain embodiments, is 0-15, 0-25, 0-50, 0-100, 0-150, 0-250, 0-500, 0-1000, 0-2500, 0-5000, 0-10,000, 0-25,000, 0-50,000 or 0-100,000 nucleotides. In certain embodiments, U has a size from 10-25, 10-50, 10-100, 10-250, 10-500, 10-1000, 10-2500, 10-5000, or 10-10,000 nucleotides.

For example, certain sequencing and microarray approaches interrogate whole samples by incorporating all DNA into a library. These methods may be "amplification-free" (as described for example by Kozarewa et al. "Amplification-free Illumina sequencing-library preparation facilitates improved mapping and assembly of (G+C)-biased genomes" Nature Methods 6:291-295 (2009); Meyer and Kircher "Illumina sequencing library preparation for highly multiplexed target capture and sequencing" Cold Spring Harb Protoc. 2010(6):pdb.prot5448 (2010). Amplification-free methods may be used reduce or avoid sampling biases during library preparation that can result in libraries that are lower in complexity than the genomic DNA from which they were derived. For such uses, N may comprise a unique sequence U of an appropriate length that is compatible with the specific procedure. In certain embodiments, N comprises $x_n U x_n$ of a length appropriate to be incorporated into the library and/or N comprises $x_n U x_n$ which is capable of hybridization to specific oligonucleotides, such as oligonucleotides immobilized on a chip or a flow cell. The specific length requirement may vary between methods. In certain embodiments, $x_n U x_n$ has a length of approximately 100, 200, 300, 400, or 500 nucleotides. In certain embodiments, $x_n U x_n$ has a length between 50-150, 100-200, 150-250, 200-300, 250-350, 300-400, 350-450, or 400-500 nucleotides. In certain embodiments, $x_n U x_n$ has a length between 10-25, 10-50, 10-100, 10-250, 10-500, 10-1000, 10-2500, 10-5000, 10-10,000, 10-25,000, 10-50,000, 10-100,000 or more nucleotides.

"L" as used herein is a linker. In certain embodiments, L is a chemical linker. The linker L associating polypeptide A with oligonucleotide N may be any chemical moiety capable of associating the two segments A and N. This linker can have any length or other characteristic and minimally comprises two reactive terminal groups that can chemically interact with (and covalently bind to) the two segments A and N. The linker may be as simple as a covalent bond, or it may be a polymeric linker many atoms in length (e.g., polyethylene, polyethylene glycol, polyamide, polyester, etc.). In certain embodiments, linker L is 1-10 atoms, 1-25 atoms, 1-50 atoms, 1-100 atoms, 1-200 atoms, 1-500, 1-1000, 1-5000, 1-10,000, 1-50,000 or 1-100,000 atoms in length. In certain embodiments, the linker is a covalent bond (e.g., a carbon-carbon bond, disulfide bond, carbon-heteroatom bond, etc.). The linker may included functionalized moieties to facilitate attachment of a nucleophile (e.g., thiol, amino) from the polypeptide segment A to the linker L. Any electrophile may be used as part of the linker. Exemplary electrophiles include, but are not limited to, activated esters, activated amides, Michael acceptors, alkyl halides, aryl halides, acyl halides, and isothiocyanates.

In certain embodiments, L is a heterobifunctional linker. In certain embodiments, N is modified to comprise one or more primary amines or thiols attached to specific bases of the nucleotides. After modification of the one or more bases in N, amine- or sulfhydryl-reactive crosslinkers can be used for their conjugation to A.

Another functional group that can be chemically modified to allow the coupling of polypeptide A to oligonucleotide N is the 5'-phosphate group. Using the 5' end of oligonucleotide N as the conjugation point by attaching a 5'-phosphate group has an advantage of keeping the remainder of the nucleic acid sequence unmodified and free to interact or easily hybridize to a complementary target (for example a primer). The alkyl phosphate may, for example, be reactive with the water-soluble carbodiimide EDC (Pierce, Rockford, Ill.), which forms a phosphate ester. Subsequent coupling to the amine-containing A segment can be performed to form a stable phosphoramidate linkage. 1-Ethyl-3-[3-dimethyl-aminopropyl]carbodiimide hydrochloride (EDC or EDAC) is a zero-length crosslinking agent used to couple carboxyl groups to primary amines. EDC reacts with a carboxyl to form an amine-reactive O-acylisourea intermediate. If this intermediate does not encounter an amine, it will hydrolyze and regenerate the carboxyl group. In the presence of N-hydroxysulfosuccinimide (Sulfo-NHS), EDC can be used to convert carboxyl groups to amine-reactive Sulfo-NHS esters. This is for example, accomplished by mixing the EDC with a carboxyl containing molecule and adding Sulfo-NHS.

If a diamine molecule is used to modify the DNA 5'-phosphate, then the resultant amine-modified oligonucleotide N can be coupled to the A segment using a heterobifunctional reagent. For example, using a diamine compound that contains a disulfide (e.g., cystamine) and then reducing the disulfide group results in a sulfhydryl that may be conjugated with A segments rendered sulfhydryl-reactive (e.g., maleimide-activated) using the heterobifunctional reagent Sulfo-SMCC (Pierce, Rockford, Ill.). Sulfosuccinimidyl-4-(N-maleimidomethyl)cyclohexane-1-carboxylate (Sulfo-SMCC) is a water-soluble, non-cleavable and membrane impermeable crosslinker. It contains an amine-reactive N-hydroxysuccinimide (NHS ester) and a sulfhydryl-reactive maleimide group. NHS esters react with primary amines at pH 7-9 to form stable amide bonds. Maleimides react with sulfhydryl groups at pH 6.5-7.5 to form stable thioether bonds. The maleimide groups of Sulfo-SMCC and SMCC are unusually stable up to pH 7.5 because of the cyclohexane bridge in the spacer arm.

Alternatively, N may be biotinylated, using e.g. photoreactive reagents. Photoactivatable biotin (Pierce, Rockford, Ill.) may be used that comprises a phenyl azide group at the end of a spacer arm and the biotin group at the other end, which allows the biotin to be non-selectively inserted into the nucleic acid structure e.g. by photolyzing.

Other methods and reagents for coupling the oligonucleotide segment N to the polypeptide segment A are well known in the art, described for example in Nitta et al., FEBS 166(1):194-198 (1984).

Polypeptide-Oligonucleotide Conjugates as Controls for Immunoprecipitations of Non-Histone Proteins:

It would be appreciated by one of skill in the art that the polypeptide-oligonucleotide conjugates of the general formula A-L-N provided herein are also suitable for generating controls and/or internal standards for immunoprecipitation assays of non-histone proteins. In certain embodiments, polypeptide-oligonucleotide conjugates described herein are provided as internal standards for antibodies raised against non-histone proteins. In certain embodiments, the polypeptide-oligonucleotide conjugates are provided as internal standards for antibodies specific for amino acid mutations of the non-histone polypeptide of interest, e.g. point mutations, antibodies specific for post-translational modifications of the non-histone polypeptide of interest, or antibodies designed to distinguish between similar epitopes.

Non-histone proteins can be for example DNA-binding proteins or chromatin-associated factors, such as transcription factors, cofactors of activator or repressor complexes, chromatin-modifying enzymes, e.g. histone acetylases, histone deacetylases, methylases, demethylases, replication factors, repair factors, etc. DNA-binding proteins or chromatin-associated factors include, but are not limited to, ASH1L, ASH2, ATF2, ASXL1, BAP1, bc110, Bmil, BRG1, CARM1, KAT3A/CBP, CDC73, CHD1, CHD2, CTCF, DNMT1, DOTL1, EHMT1, ESET, EZH1, EZH2, FBXL10, FRP(Plu-1), HDAC1, HDAC2, HMGA1, hnRNPA1, hp1 gamma, Hset1b, Jarid1A, Jarid1C, KIAA1718_JHDM1D, KAT5, KMT4, LSD1, NFKB P100, NSD2, MBD2, MBD3, MLL2, MLL4, P300, pRB, RbAP46/48, RBP1, RbBP5, RING1B, RNApolII P S2, RNApolII P S5, ROC1, sap30, setDB1, Sf3b1, SIRT1, Sirt6, SMYD1, SP1, SUV39H1, SUZ12, TCF4, TET1, TRRAP, TRX2, WDR5, WDR77, YY1. Commercial antibodies are available for all of these factors.

Specific posttranscriptional modifications include but are not limited to phosphorylation, acetylation, and ubiquitination. For example, the polypeptide-oligonucleotide conjugates may serve as controls for p53-specific modifications, such as phospho-serine 6, phospho-threonine 18, acetyl-lysine 373, acetyl-lysine 382, phosphor-serine 392, or pRB-specific modifications, such as phospho-serine 601, phospho-serine 605, phospho-serine 773, acetyl-873, and acetyl-874. Such controls may be generated according to the teachings provided herein. The polypeptide-oligonucleotide conjugates of the general formula A-L-N may comprise A comprising $X_nY[M]X_n$ and N comprising $x_nP1-U—P2x_n$ or $x_nUx_n$ as described herein. Non-limiting examples for A of p53 modification-specific controls are: $X_nS[ph]X_n$, $X_nT[ph]X_n$, and $X_nK[ac]X_n$, wherein X is any amino acid, preferably an amino acid derived from p53 amino acid sequence. For example, A specific for human p53 phospho-serine 6 may comprise 1, 2, 3, 4, 5, 6, 7, 8, 9, 10, 11, 12, 13, 14, 15, 16, 17, 18, 19, 20, or more amino acids of the human p53 amino acid sequence, such as

```
                                              (SEQ ID NO: 60)
MEEPQS[ph]DPSV EPPLSQETFS DLWKLLPENN, (SEQ ID NO: 61)
PQS[ph]DPS, (SEQ ID NO: 62)
QS[ph]DPSV EPPLSQ,
and (SEQ ID NO: 63)
MEEPQS[ph]D.
```

A specific for human p53 acetyl-lysine 373, may comprise 1, 2, 3, 4, 5, 6, 7, 8, 9, 10, 11, 12, 13, 14, 15, 16, 17, 18, 19, 20, or more amino acids of the human p53 amino acid sequence, such as

```
                                              (SEQ ID NO: 64)
GSRAHSSHLK SKK[ac]GQSTSRH KKLMFKTEGP DSD, (SEQ ID NO: 65)
SKK[ac]GQ,
```

```
                                              (SEQ ID NO: 66)
HLK SKK[ac]GQSTSRH,
and (SEQ ID NO: 67)
K[ac]G.
```

A specific for human pRb acetyl-873, and acetyl-874, may comprise 1, 2, 3, 4, 5, 6, 7, 8, 9, 10, 11, 12, 13, 14, 15, 16, 17, 18, 19, 20, or more amino acids of the human pRb amino acid sequence, such as

```
                                              (SEQ ID NO: 68)
TSEKFQKINQ MVCNSDRVLK RSAEGSNPPK PLK[ac]K[ac]
LRFDIE GSDEADGSKH LPGESKFQQK, (SEQ ID NO: 69)
PLK[ac]K[ac]LRFD,
and (SEQ ID NO: 70)
PPK PLK[ac]K[ac]LRFDIE GSDEADGS.
```

In certain embodiments, A comprises more than 20 amino acids of the DNA-binding protein or chromatin-associated factor that may comprise a specific amino acid modification. In certain embodiments, A comprises is 25, 50, 75, 100, 250, 500, 1000, 2500, 5000, 10,000, 25,000, or 50,000 amino acids of the DNA-binding protein, chromatin-associated factor or protein complexes thereof (e.g. multi-subunit comprising chromatin-remodeling complexes). In certain embodiments, A comprises the amino acids of the full-length DNA-binding protein or chromatin-associated factor.

As described herein, N may comprise a unique sequence and primer sequences, e.g. $x_nP1-U—P2x_n$, wherein the unique sequence may be used to identify the specific amino acid modification represented in A. In certain embodiments, N does not comprise an amplification sequence (e.g. P1 and P2) and comprises a unique sequence $x_nUx_n$ that may be used to identify the specific amino acid modification represented in A. One of ordinary skill would appreciate that polypeptide-oligonucleotide conjugates may be generated that represent specific posttranscriptional modifications or specific mutations for any polypeptide of interest for which such modifications and/or mutations are known.

For many of the commercially available antibodies specific for DNA-binding proteins or chromatin-associated factors their suitability in immunoprecipitation assays is unknown. Controls and internal standards that could be used to test the suitability of such antibodies are generally not available. Using existing controls is often costly and time consuming because data about the genomic regions that are bound by the DNA-binding proteins and chromatin-associated factors is not always available. Such lack of information requires the generation of multiple primers specific for different genomic regions and/or requires performing ChIP-Seq assays. To overcome these limitations, the polypeptide-oligonucleotide conjugates described herein may be used as internal standards for any experiment involving antibodies specific for non-histone proteins, such as DNA-binding proteins and chromatin-associated factors. In certain embodiments, the polypeptide-oligonucleotide conjugates described herein may be used for immunoprecipitation experiments. In other embodiments, the polypeptide-oligonucleotide conjugates described herein may be used as internal standards for comparing and/or using data obtained from any type of suitable assay or experiment in combination with data obtained from ChIP, e.g. when using antibodies specific for DNA-binding proteins and chromatin-associated factors. The polypeptide-oligonucleotide conjugates described herein may be used as internal standards for normalization purposes (as described herein), for example, when measuring the effect of a gene "knock-down" on a cell (such as by an antisense or RNAi-mediated knock-down, by a knock-out mutation, or by a misregulated cellular pathway) and comparing the ChIP data obtained from the knock-down cell with the ChIP data obtained from a wild-type cell. It would be understood by one of ordinary skill that the polypeptide-oligonucleotide conjugates described herein may be used in circumstances not involving knock-down, such as, for example, in circumstances when a DNA-binding protein and chromatin-associated factor is modified differently (e.g. post-transcriptionally modified) in any two cells. The two cells may be of different cell type, the same cell type but derived from different tissue or from a different species, or may be derived from a wild-type and a mutant cell (e.g. a normal cell/cancer cell pair).

Polypeptide/Polynucleotide-Oligonucleotide Conjugates as Controls for Immunoprecipitations of Non-Histone Proteins:

Other aspects of the invention relate to control agents for immunoprecipitation (IP) assays, including but not limited to RNA-IP followed by sequencing (RIP-seq), methylated-DNA IP followed by sequencing (mDIP-seq), bisulphite sequencing (BS-seq), High-throughput sequencing of RNA isolated by crosslinking IP (HITS-CLIP), formaldehyde-assisted isolation of regulatory elements followed by sequencing (FAIRE-seq), and micrococcal nuclease digestion followed by sequencing (MNase-seq). Control agents provided herein comprise the formula:

X—B or B—X, where X is a molecule (e.g., polypeptide, such as A described above, or a polynucleotide), and B (also referred to as "barcode") is an oligonucleotide (e.g., DNA or RNA) comprising, for example, 10 nucleotides, wherein the sequence of nucleotides of B uniquely identifies X. In some configurations, a linker L is used to conjugate B and X. Examples of control agents include, but are not limited to, barcoded DNA-peptide conjugates, barcoded RNA-peptide conjugates, barcoded methylated DNA oligos, and assembled nucleosomes conjugated to barcoded DNA.

Polypeptide-Oligonucleotide Conjugates as Validation Tools for Screening ChIP-Capable Antibodies:

For ChIP assays, it is advantageous to fully characterize the antibodies used in the assay. Antibodies used in ChIP assays typically recognize histones, histone modifications or chromatin-associated factors. One common method of characterizing antibody specificity (epitope recognition) employs assays involving peptide competition (using target and non-target antigens as competitors) in both ELISA and Western blot. Western blotting can also be used to demonstrate that the correct target has been successfully immunoprecipitated. Calf thymus histone preparations are often used as a positive control histone sample for validating antibody specificity in Western blot. Immunofluorescence can be used to validate that antigen recognition occurs in a cellular context, and can also be combined with competition assays.

However, even full characterization will not necessarily provide sufficient information about the antibody's suitability for, and specificity in ChIP, as the effects of cross-linking can significantly alter (native) epitopes and/or may lead to the loss of specific epitopes. Further, the binding affinity of certain may decrease dramatically under more stringent buffer conditions (that are commonly used in ChIP assays, e.g. high salt and/or detergent conditions) that increase antibody specificity.

Specific antibodies for ChIP should be affinity-purified, e.g. when the antibody is a monoclonal antibody (raised against a specific epitope). Many laboratories use sera (e.g. polyclonal antibody population that recognize different epitopes) as their antibody source and inherent background problems are overcome by using highly stringent buffers.

A stringent test for the suitability of an antibody for ChIP is to perform parallel ChIP assays in wild-type and mutant or modified and unmodified backgrounds to demonstrate that the observed enrichment is due solely to the target antigen. Such tests are difficult to perform with the controls that are currently available.

The polypeptide-oligonucleotide conjugates of the general formula A-L-N that may comprise A comprising $X_nY[M]X_n$ and N comprising $x_nP1$-U-$P2x_n$ or $x_nUx_n$ as described herein may be used to provide specific epitopes to screen novel and/or untested antibodies for their suitability in ChIP assays. For example, a pool (library) of the polypeptide-oligonucleotide conjugates provided herein specific for different histone modifications may be used in a mock-ChIP assay, under conditions similar or identical to those actually used in a ChIP assay using genomic material, to screen and/or validate antibodies for their specificity and/or affinity to specific histone modifications. Such a pool may comprise polypeptide-oligonucleotide conjugates of the general formula A-L-N comprising A segments that comprise antigens representing mono-methylated H3K4, mono-methylated H3K9, mono-methylated H3K27, mono-methylated H3K79, di-methylated H3K79, tri-methylated H3K4, acetylated H3K9, acetylated H3K14, tri-methylated H3K9 and tri-methylated H3K27. An antibody may be screened for suitability in a ChIP assay using such pool (library) by contacting the antibody with the polypeptide-oligonucleotide conjugate pool under conditions similar or identical to those actually used in a ChIP assay using genomic material. If the antibody is for example specific for mono-methylated H3K9, a subsequent sequence analysis and quantification of the precipitated fraction (e.g. by qPCR) would produce a statistically significant overrepresentation of the unique nucleotide sequence (of N) that is linked via the linker L to the A segment comprising the antigen representing mono-methylated H3K9. All other unique sequences linked to the A segments comprising the antigens representing the other histone modifications would be underrepresented in a statistically significant manner. Antibodies with low affinity and/or low specificity may produce signals that are not statistically significant, e.g. over background or over the signal derived from the other polypeptide-oligonucleotide conjugates representing the non-desired antigens.

Provided herein are thus screening methods using the polypeptide-oligonucleotide conjugates described herein to screen antibodies for their suitability in ChIP assays, wherein antibodies that produce a significant overrepresentation of a signal specific to a single amino acid modification or specific to a combination of histone modifications in conditions similar or identical to those actually used in a ChIP assay using genomic material are considered suitable for use in ChIP assays.

It would be appreciated by one of ordinary skill that the use of the polypeptide-oligonucleotide conjugates described herein to screen antibodies is not limited to ChIP assays and histone modifications. The polypeptide-oligonucleotide conjugates described herein may be used to screen antibodies for suitability in immunoprecipitation assays of any non-histone polypeptide, for example using A segments comprising antigens representing specific post-translational modification (e.g. phosphorylation, acetylation, ubiquitination, etc.) of the non-histone polypeptide of interest or antigens representing one or more specific point mutation(s) within the amino acid sequence of the non-histone polypeptide of interest and/or the appropriate antigen representing the non-modified and non-mutated forms.

Use of Polypeptide-Oligonucleotide Conjugates to Normalize ChIP and Other Assay Data and to Quantify Experimental Parameters of ChIP Assays:

Variations in the starting material (quantity and/or quality) in ChIP assays are possible. ChIP data may therefore be normalized for the amount of starting material, e.g. to avoid errors introduced due to uneven sample quantities. To normalize the data obtained, the final amplification value may be divided by the amplification value of input material. For example, one may take a sample of the lysed starting material for PCR of control regions in parallel with the eluted material from the ChIP assay. It is possible that certain regions of the genome are precipitated more effectively or amplify better than others. Further, there is the possibility of nucleosome rearrangement during fragmentation (e.g. enzymatic fragmentation). PCR primers may therefore be generated specific for several regions in the starting material, as well as for the purified/immuno-precipitated material, as controls. Normalization is also difficult in microarray and sequencing assays. Such assays could also be improved by providing internal standards, such as the agents provided herein.

The polypeptide-oligonucleotide conjugates of the general formula A-L-N that may comprise A comprising $X_nY[M]X_n$ and N comprising $x_nP1-U—P2x_n$ or $x_nUx_n$ as described herein may be used to provide quantifiable controls and/or internal standards. The polypeptide-oligonucleotide conjugates described herein may be provided as a pool in which the concentration of each individual polypeptide-oligonucleotide conjugate is accurately known or individually at a known concentration. For example, a pool of or an individual polypeptide-oligonucleotide conjugate(s) of known concentration may be used as an input control, as a process control without genomic sample material and/or may be "spiked" into the samples of fragmented genomic material. The starting concentration of the polypeptide-oligonucleotide conjugate(s) in each case is known or can be calculated. The polypeptide-oligonucleotide conjugates that may comprise A comprising $X_nY[M]X_n$ and N comprising $x_nP1-U—P2x_n$ provide a signal amplification of the unique nucleic acid sequence U that is independent of variations in chromatin, since U may be designed in such way that it is of one particular length (e.g. 10, 20, 30, 40, 50, or more nucleotides) that is the same for each unique sequence U and P1 and P2 may be the same sequence(s) for each polypeptide-oligonucleotide conjugate. In certain embodiments, N does not comprise an amplification sequence (e.g. P1 and P2) and comprises a unique sequence $x_nUx_n$. The magnitude of the signal obtained (e.g. from qPCR, hybridization, sequencing or other quantification method) for the immuno-precipitated polypeptide-oligonucleotide conjugates may then depend only on the conditions used for the ChIP assay and on the specificity and/or affinity of the antibody for the antigen ($X_nY[M]X_n$) represented by the A segment. To normalize the signal obtained for the immuno-precipitated polypeptide-oligonucleotide conjugates, the final amplification value may be divided by the amplification value of input polypeptide-oligonucleotide conjugates. Provided herein are thus methods for quantifying one or more experimental parameters of ChIP assays using the polypeptide-oligonucleotide conjugates described herein. Such experimental parameters include but are not limited to, sample loss, immunoprecipitation efficiency, quality of the starting/input material (e.g. fragmented genomic material), relative fold enrichment of the antigen-specific signal for the immuno-precipitated sample. Provided herein are also methods of normalizing the signal obtained for the immuno-precipitated genomic material using the polypeptide-oligonucleotide conjugates described herein.

Kits Comprising Polypeptide-Oligonucleotide Conjugates for ChIP Assays:

Provided herein are kits for chromatin immunoprecipitation (ChIP) assays. In certain embodiments, such kits comprise the polypeptide-oligonucleotide conjugates of the formula A-L-N, as described herein, and one or more other chemical reagents necessary to perform a ChIP assay and/or chemical reagents necessary to perform subsequent analysis, e.g. PCR, hybridization, or sequencing. Such kits may contain one or more enzymes necessary to perform the ChIP assay, for example, RNaseA and Proteinase K; one or more solutions and buffers, such as, formaldehyde, glycine, PBS, cell lysis buffer, Triton X-100, protease inhibitor cocktails, wash buffers elution buffers; antibodies (specific and control); and hardware, such as magnetic beads and multi-well plates. Such kits may contain one or more enzymes necessary to perform chromatin fragment modification (e.g. addition of adapters) and subsequent Real Time PCR or sequencing, for example, Klenow DNA polymerase, DNA polymerase, T4 ligase, T4 polynucleotide kinase, T4 DNA polymerase, Klenow fragment 3' to 5' exo minus; one or more solutions and buffers, such as, enzyme reaction buffers, dATP, dNTPs, ultrapure water, TE; PCR or sequencing specific adapters, PCR or sequencing primers; and hardware, such as e.g. DNA purification columns and multi-well plates. In certain embodiments, kits may be provided comprising one or more polypeptide-oligonucleotide conjugates of the formula A-L-N, as described herein, specific for one or more particular ChIP targets, e.g. histone modifications, unmodified histones, or chromatin-associated factors (transcription factors, histone acetylases, histone deacetylases, methylases, demethylases, repressor/activator co-factors, polymerases, DNA repair enzymes, etc.). In certain embodiments, a pool of 1, 5, 10, 15, 20, 25, 30, 35, 40, 45, 50, 55, 60, 65, 70, 75, 80, 85, 90, 95, 100 or more different polypeptide-oligonucleotide conjugates of the formula A-L-N may be provided. For example, a pool may comprise one or more polypeptide-oligonucleotide conjugates

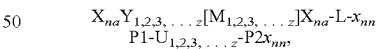

wherein "X" is an amino acid; "na" is a number of amino acids; $Y_1, Y_2, Y_3 \ldots z$ are "z" number of different modified amino acids; $M_1, M_2, M_3 \ldots z$ are "z" number of different modifications; "L" is a linker; "x" is any nucleotide, "nn" is a number of nucleotides, P1 and P2 are primer sequences, and $U_1, U_2, U_3 \ldots z$ are "z" number of unique nucleotide sequences of, wherein "z" is the number of different polypeptide-oligonucleotide conjugates in the pool, e.g. 1, 5, 10, 15, 20, 25, 30, 35, 40, 45, 50, 55, 60, 65, 70, 75, 80, 85, 90, 95, 100 or more. In certain embodiments, the primer sequences P1 and P2 are independently 10-35, 10-40, 10-45, 10-50, 10-55, 10-60, 10-65, 10-70, 10-75, 10-100, 10-250, 10-500, or 10-1000 nucleotides long. "na" in certain embodiments, is 0-15, 0-25, 0-50, 0-100, 0-150, 0-250, 0-500, 0-1000, 0-2500, 0-5000, 0-10,000, 0-25,000, or 0-50, 000 amino acids. "nn" in certain embodiments, is 0-15, 0-25, 0-50, 0-100, 0-150, 0-250, 0-500, 0-1000, 0-2500, 0-5000, 0-10,000, 0-25,000, 0-50,000, 0-100,000 nucleotides. In certain embodiments, U has a size from 10-25, 10-50, 10-100, 10-250, 10-500, 10-1000, 10-2500, 10-5000, or 10-10,000 nucleotides. In certain embodiments, N does not comprise an amplification sequence (e.g. P1 and P2) and comprises a unique sequence $x_nUx_n$.

The pools of polypeptide-oligonucleotide conjugates may represent 1, 5, 10, 15, 20, 25, 30, 35, 40, 45, 50, 55, 60, 65, 70, 75, 80, 85, 90, 95, 100 or more different histone modifications, including but not limited to 1) modifications for Histone H1, such as H1 (phospho S1+T3), H1 (phospho S35), H1 (acetyl K63);

2) modifications for Histone H2A, such as H2A (asymmetric di methyl R3), H2A (symmetric di methyl R3), H2A (acetyl K5), H2A (mono methyl R17), H2A (symmetric di methyl R77), H2A (Hydroxy P26), H2A (mono methyl K125), H2A (tri methyl K125), H2A (mono methyl K127), H2A (tri methyl K127), H2A (phospho S129);

3) modifications for Histone H2B, such as H2B (acetyl K5), H2B (di methyl K5), H2B (Hydroxy P10), H2B (di methyl K43);

4) modifications for Histone H3, such as H3 (mono methyl R2), H3 (citrulline 2+8+17), H3 (mono methyl K4), H3 (di methyl K4), H3 (tri methyl K4), H3 (di+tri methyl K4), H3 (acetyl K9), H3 (acetyl K9, phospho S10), H3 (mono methyl K9), H3 (di methyl K9), H3 (tri methyl K9), H3 (phospho S10), H3 (asymmetric di methyl R17), H3 (acetyl K18), H3 (acetyl K27), H3 (di methyl K27), H3 (tri methyl K27), H3 (mono methyl K27, tri methyl K27+K4), H3 (mono methyl K36), H3 (tri methyl K36), H3 (Hydroxy P38), H3 (mono methyl K79), H3 (di methyl K79), H3 (tri methyl K79), H3 (mono+di+tri methyl K79), H3 (Hydroxy P121), H3 (tri methyl K122); and 5) modifications for Histone H4, such as H4 (symmetric di methyl R3), H4 (acetyl K8), H4 (acetyl K12), H4 (mono methyl K20), H4 (tri methyl K20), H4 (phospho T30), H4 (Hydroxy P32), H4 (tri methyl K59), H4 (phospho T80), H4 (acetyl K91), H4 (phospho T96).

It should be appreciated that kits comprising polypeptide-oligonucleotide conjugates comprising A segments that comprise antigens of non-histone polypeptides, as described herein, may also be provided. Such kits may comprise pools of polypeptide-oligonucleotide conjugates comprising A segments that comprise antigens of, for example, p53-specific post-translational modifications, e.g. phosphorylated Ser 6, Ser 9, Ser 15, Thr 18, Ser 20, Ser 33, Ser 37, Ser 46, Thr 55, Thr 155, Ser 315, and/or Ser 392.

Figure 4:
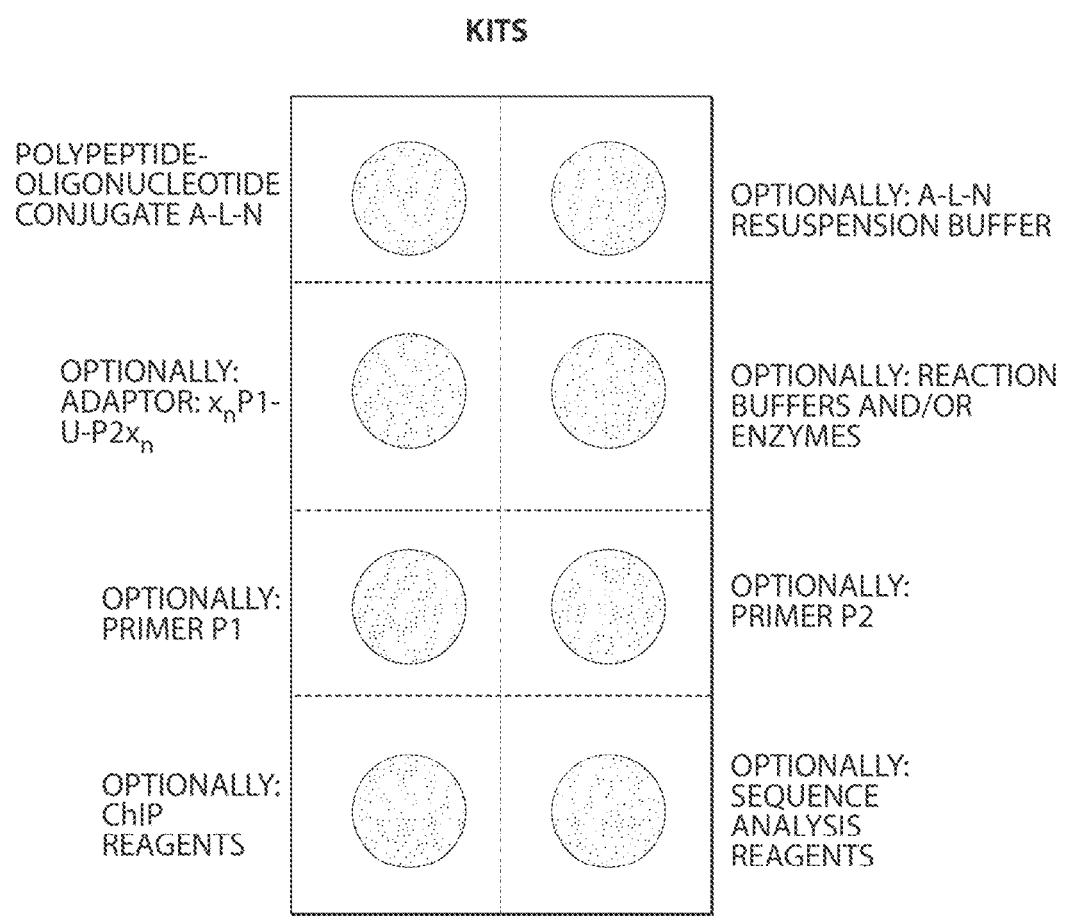
FIG. 4 is a schematic depicting various kits. The circles represent one or more receptacles for one or more reagents. The dotted lines represent various expanded kits that further contain optional receptacles/reagents that may be combined in any number or order with the polypeptide-oligonucleotide conjugate A-L-N.

Pools of polypeptide-oligonucleotide conjugates may be provided individually that is without any other reagent, e.g. as an accessory for ChIP assays, or may be provided together with agents necessary to perform ChIP assays (e.g. antibodies, cross-linking, binding, washing, elution buffers, etc.) and/or subsequent with agents necessary to perform subsequent assays of nucleic acid analyses (e.g. PCR amplification, sequencing, hybridization, etc.) as depicted in FIG. 4. The polypeptide-oligonucleotide conjugates may be provided lyophilized or in suspension (e.g. in a suitable buffer). If the polypeptide-oligonucleotide conjugates are provided in lyophilized form, a suitable suspension buffer may also be provided with the kit.

The polypeptide-oligonucleotide conjugates may be used in any ChIP assay. ChIP assays may be used to analyze the spatial and temporal dynamics and interactions of chromatin and its associated factors, which can be, for example, detected at a single promoter or over the entire human genome. ChIP assays are based on the selective enrichment of a chromatin fraction containing a specific antigen. Antibodies that recognize a protein (e.g. a chromatin-associated factor such as a transcription factor) or protein modification (e.g. a histone tail modification) of interest can be used to determine the relative abundance of that antigen at one or more locations (loci) in the genome. It is more common to analyze euchromatin, which is though to contain active genes and to maintain an "open" and "extended" chromatin. Heterochromatin, which is thought to contain many inactive genes and repetitive DNA sequences and is thought to be in a "condensed" state is generally more difficult to analyze by ChIP.

Generally, ChIP assays can be used to determine whether a given protein binds to a specific location on the chromatin in vivo or if a specific histone modification is present at a specific location on the chromatin at the time of analysis. ChIP may be used to selectively enrich for DNA sequences bound by a particular protein (e.g. transcription factor or histone) in living cells by cross-linking DNA-protein complexes and using an antibody that is specific against a protein of interest. Specific ChIP protocols are well known in the art. The ChIP procedure may consists of the following steps:

(a) (optionally) cross-linking of chromatin in vivo (to immobilize the antigen of interest to its chromatin binding site)

(b) isolation of total chromatin (c) fragmentation of the chromatin isolated in (b)

(d) immunoprecipitation of the chromatin fragments obtained in (c)

(e) analysis of the immunoprecipitated fraction obtained in (d) to determine the amount of a target DNA sequence relative to its abundance in the input chromatin.

The quantitative analysis is typically carried out using PCR, sequencing or hybridization-based techniques. Such procedures are well now in the art and, for example, Allis & Wu ((Eds). (2004) "Chromatin and chromatin remodelling enzymes", Methods in Enzymology v376, Elsevier Academic Press, 2004) provide a review of the procedures and methodologies of ChIP.

The polypeptide-oligonucleotide conjugates described herein may comprise an N segment comprising $x_nP1-U—P2x_n$. It may therefore be particularly useful to modify the immuno-precipitated genomic fraction obtained through the ChIP assay in such way as to link nucleotides of the sequence of P1 and P2 to the obtained nucleic acid fragments. This may allow amplification and/or quantification using the same primers for the control (e.g. the polypeptide-oligonucleotide conjugates described herein) and the immuno-precipitated genomic material. Use of the same primers may reduce or eliminate unwanted variations in signal obtained in the amplification and/or quantification assays. In certain embodiments, N does not comprise an amplification sequence (e.g. P1 and P2) and comprises a unique sequence $x_nUx_n$.

Generally, to analyze the immunoprecipitated fraction of fragmented chromatin (genomic DNA), the DNA fragments may be eluted and purified (e.g. by phenol/chloroform extraction-ethanol precipitation or affinity purification using silica beads, such as QIAgen (Germantown, Md.) DNA purification kits: e.g. QIAquick™ column) and may be further modified to allow amplification and/or sequencing (e.g. from the same primers P1 and P2 provided in the polypeptide-oligonucleotide conjugates described herein). Common modification steps include:

(a) performing end repair: to convert the overhangs resulting from fragmentation into blunt ends, using e.g. T4 DNA polymerase and *E. coli* DNA polymerase I Klenow fragment. The 3' to 5' exonuclease activity of these enzymes removes 3' overhangs and the polymerase activity fills in the 5' overhangs, (b) addition of 'A' bases to the 3' end of the DNA fragments: to add an 'A' base to the 3' end of the blunt phosphorylated DNA fragments, using the polymerase activity of e.g. Klenow fragment (3' to 5' exo minus). This may be performed to prepare the DNA fragments for ligation to adapters that have a single 'T' base overhang at their 3' end, (c) ligation of adapters to DNA fragments, e.g. using DNA ligase (d) purification of ligation products: to remove any unligated adapters or any adapters that may have ligated to one another, using e.g. gel purification, (e) enrichment of the adapter-modified DNA fragments by PCR: to selectively enrich DNA fragments that have adapter molecules on both ends and to amplify the amount of DNA, (f) validation and analysis of the obtained library.

For validation and analysis chromatin immunoprecipitation-massively parallel DNA sequencing (ChIP-Seq) may be used. It can be used to precisely map global DNA binding sites for any protein of interest, e.g. transcription factor, restriction enzyme, or other chromatin associated proteins, on a genome scale. ChIP-DNA fragments are sequenced simultaneously using a genome sequencer. A single sequencing run can scan for genome-wide associations with high resolution. Massively parallel sequence analyses may be used in conjunction with whole-genome sequence databases to analyze the interaction pattern of a protein of interest (e.g. transcription factors, polymerases or transcriptional machinery) with DNA (Johnson et al. (2007) *Science* 316:1497-1502), or to analyze the pattern of an epigenetic chromatin modification of interest (e.g. histone modifications or DNA modifications). Massively parallel sequencing is known in the art and many sequencing methods may be used. Some technologies may use cluster amplification of adapter-ligated ChIP DNA fragments on a solid flow cell substrate. The resulting high density array of template clusters on the flow cell surface may then be submitted to sequencing-by-synthesis in parallel using for example fluorescently labeled reversible terminator nucleotides. Templates are sequenced base-by-base during each read. The resulting data may be analyzed using data collection and analysis software that aligns sample sequences to a known genomic sequence.

Chromatin immunoprecipitation may also be combined with microarray "ChIP-on-chip," which requires a hybridization array. ChIP-on-chip may require large sets of tiling arrays (of overlapping probes designed to densely represent a genomic region of interest). Tiling arrays that may be used with the polypeptide-oligonucleotide conjugates described herein may comprise oligonucleotides comprising a sequence to which N is at least in part complementary. These complementary sequences may be of a length sufficient to allow specific hybridization between parts or all of the nucleotide sequence provided by N and the oligonucleotide on the tiling array. In certain embodiments, wherein N comprises $x_nUx_n$, all or parts of the unique sequence U is complementary to the oligonucleotide on the tiling array. The polypeptide-oligonucleotide conjugates described herein may then be quantified using such tiling arrays. Upon acquisition of data (readout), for example by sequencing or hybridization, the relative representation of the different polypeptide-oligonucleotide conjugates described herein may be evaluated by comparing their representation a) within a given sample and/or b) with a control sample(s). Enrichment ratios may then be calculated for each polypeptide-oligonucleotide conjugate. These ratios may then be used to estimate or calculate the degree to which the corresponding antigen (represented by the polypeptide-oligonucleotide conjugate) was enriched by the immunoprecipitation assay and thereby evaluating the efficacy of the experiment in quantitative terms, such as, for example, sensitivity and/or specificity.

Additional Embodiments

Also contemplated herein are other control agents for other immunoprecipitation (IP) assays, as set forth below. An internal standard for a particular IP assay may have the formula:

X—B or B—X, where X is a molecule (e.g., polypeptide, such as A described above, or a polynucleotide), and B (also referred to as "barcode") is an oligonucleotide (e.g., DNA or RNA) comprising, for example, 10 nucleotides, wherein the sequence of nucleotides of B uniquely identifies X. In some configurations, a linker L is used to conjugate B and X.

RNA Immunoprecipitation (RIP)-RNA-Sequencing (RNA-seq) (RIP-seq)

In some embodiments, the internal controls described herein may be used in RIP-seq assays. RIP is similar to ChIP described above, except rather than targeting DNA binding proteins as in ChIP, RIP targets RNA binding proteins. In some embodiments, live cells may be lysed and the immunoprecipitation can be performed with an antibody that targets a protein of interest. By isolating the protein, the RNA will also be isolated as it is bound to the protein. In some embodiments, the purified RNA-protein complexes can be separated by performing an RNA extraction and the identity of the RNA can be determined by cDNA sequencing (RNA-seq) or RT-PCR. In certain embodiments, some variants of RIP, such as PAR-CLIP include cross-linking steps, which then may require less careful lysis conditions. Internal controls for use with an RIP-seq assay include barcoded RNA-peptide conjugates, for example, having the configuration X—B, where X is an RNA-binding protein, and B is an oligonucleotide of cDNA that uniquely identifies X.

Methylated-DNA Immunoprecipitation (meDIP or mDIP)-Sequencing

In some embodiments, the internal controls described herein may be used in mDIP-sequencing. mDIP is a large-scale (chromosome- or genome-wide) technique that can be used to enrich for methylated DNA sequences. In certain embodiments, the method comprises isolating methylated DNA fragments via an antibody raised against 5-methylcytosine (5mC). In some embodiments, a purified fraction of methylated DNA can be input to high-throughput DNA detection methods such as high-resolution DNA microarrays (MeDIP-chip) or next-generation sequencing (MeDIP-seq). Internal controls for use with an MeDIP-seq assay include barcoded methylated DNA oligonucleotides, for example, having the configuration X—B, where X is a methylated DNA oligonucleotide, and B is an oligonucleotide of DNA that uniquely identifies X.

MethylC-Sequencing or Bisulphite (BS)-Sequencing

In some embodiments, the internal controls described herein may be used in BS-sequencing (BS-seq). Bisulfite sequencing is the use of bisulfite treatment of DNA to determine its pattern of methylation. Treatment of DNA with bisulfite converts cytosine residues to uracil, but leaves 5-methylcytosine residues unaffected. Thus, bisulfite treatment introduces specific changes in the DNA sequence that depend on the methylation status of individual cytosine residues, yielding single-nucleotide resolution information about the methylation status of a segment of DNA. In some embodiments, BS-seq applies routine or "shotgun" sequencing methods on bisulfite-treated genomic DNA to determine methylation status at CpG dinucleotides. Internal controls for use with a BS-seq assay include barcoded methylated DNA oligonucleotides, for example, having the configuration X—B, where X is a methylated DNA oligonucleotide, and B is an oligonucleotide of DNA that uniquely identifies X.

High-Throughput Sequencing of RNA Isolated by Cross-linking Immunoprecipitation (HITS-CLIP)

In some embodiments, the internal controls described herein may be used in HITS-CLIP (also known as CLIP-seq) assays. HITS-CLIP is a genome-wide means of mapping protein-RNA binding sites. HITS-CLIP is similar to ChIP-seq, except that proteins bound to RNA (e.g., splicing factors) are immune-precipitated and the RNA fragments are sequenced. Internal controls for use with a HITS-CLIP-seq assay include barcoded RNA-peptide conjugates, for example, having the configuration X—B, where X is an RNA-binding protein, and B is an oligonucleotide of cDNA that uniquely identifies X.

Formaldehyde-Assisted Isolation of Regulatory Elements (FAIRE)-Sequencing

In some embodiments, the internal controls described herein may be used in FAIRE-sequencing. DNA segments that actively regulate transcription in vivo are typically characterized by eviction of nucleosomes from chromatin and are experimentally identified by their hypersensitivity to nucleases. FAIRE refers to a method of isolating nucleosome-depleted DNA from chromatin. In some embodiments, the method comprises crosslinking chromatin with formaldehyde in vivo (in cells), shearing the cells by sonication, extracting the chromatin/DNA by phenol-chloroform extracted. The DNA recovered in the aqueous phase, in some embodiments, is subjected to high-throughput sequencing (FAIRE-seq). Internal controls for use with an FAIRE-seq assay include barcoded DNA oligonucleotides, for example, having the configuration X—B, where X is a DNA oligonucleotide, and B is an oligonucleotide of DNA that uniquely identifies X.

Micrococcal Nuclease Digestion (MNase)-Sequencing

In some embodiments, the internal controls described herein may be used in MNase-sequencing. MNase is a method that A method that distinguishes nucleosome positioning based on the ability of nucleosomes to protect associated DNA from digestion by micrococcal nuclease. In some embodiments, protected fragments may be sequenced to produce genome-wide maps of nucleosome localization. Internal controls for use with an MNase-seq assay include in vitro assembled nucleosomes conjugated to barcoded DNA oligonucleotides, for example, having the configuration X—B, where X is an assembled nucleosome, and B is an oligonucleotide of DNA that uniquely identifies X.

Other aspects and embodiments of the invention are further described in international application number PCT/US2011/054072, filed Sep. 29, 2011, which claims the benefit under 35 U.S.C. §119(e) of U.S. provisional application Ser. No. 61/387,689, filed Sep. 29, 2010, each of which is incorporated by reference herein in its entirety. The following numbered paragraphs also provide various other aspects and embodiments contemplated by the invention:

1. A chromatin immunoprecipitation method for parallel processing of multiple samples, the method comprising: (a) cross-linking a chromatin-associated factor to chromatin; (b) shearing the cross-linked chromatin of (a) to provide nucleic acid fragments; (c) contacting the chromatin-associated factor cross-linked to the nucleic acid fragments of (b) with a first affinity molecule; (d) releasing the nucleic acid from the chromatin-associated factor and from the first affinity molecule; (e) contacting the released nucleic acid fragments in (d) with a second affinity molecule; (f) releasing the nucleic acid fragments from the second affinity molecule, and (g) optionally isolating the nucleic acid fragments, and (h) optionally analyzing the distribution and enrichment of the isolated nucleic acid fragments, wherein the first affinity molecule and/or second affinity molecule optionally is coupled to a substrate suitable for parallel processing of multiple samples.

2. The method of paragraph 1, wherein contacting the nucleic acid fragments in (e) is carried out using an affinity interaction between the nucleic acid fragment and the second affinity molecule.

3. The method of paragraph 2, wherein the nucleic acid is suitably modified for this interaction.

4. The method of paragraph 3, wherein the modification is addition of poly-A tails or biotinylation.

5. The method of any one of paragraphs 1 to 4, wherein the second affinity molecule is a poly-T oligonucleotide, avidin or streptavidin.

6. The method of any one of paragraphs 1 to 5, wherein the second affinity molecule is silica.

7. The method of any one of paragraphs 1 to 6, wherein the substrate is a surface of a bead or a well.

8. The method of paragraph 7, wherein the bead is a magnetic bead.

9. The method of any one of paragraphs 1 to 8, wherein steps (e) and (f) are not carried out using a purification column or using phenol/chloroform extraction and ethanol precipitation.

10. The method of paragraph 6, wherein steps (e) and (f) are not carried out using a purification column comprising silica.

11. The method of any one of paragraphs 1 to 10, wherein the format is a 6-well plate, a 12-well plate, a 24-well plate, a 96-well plate, a 384-well plate or a 1536-well plate.

12. The method of any one of paragraphs 1 to 11, wherein the first affinity molecule in step (c) is an antibody that specifically binds a chromatin-associated factor cross-linked to the nucleic acid fragment.

13. The method of paragraph 12, wherein the antibody is coupled to a substrate.

14. The method of paragraph 13, wherein the substrate is a surface of a bead or a well.

15. The method of paragraph 13 or paragraph 14, wherein the substrate comprises protein A or protein G.

16. The method of any one of paragraphs 13 to 15, wherein the chromatin-associated factor binds to the antibody before the antibody is coupled to the substrate.

17. The method of any one of paragraphs 1 to 16, wherein the chromatin-associated factor comprises an affinity tag.

18. The method of paragraph 17, wherein the affinity tag is FLAG-tag, myc-tag, biotin or DHFR.

19. The method of paragraph 17 or paragraph 18, wherein the affinity molecule is an antibody that specifically binds the affinity tag, avidin or streptavidin.

20. The method of paragraph 19, wherein the antibody is an anti-FLAG antibody, or an anti-myc antibody.

21. The method of any one of paragraphs 1 to 20, wherein shearing in step (b) is carried out by sonication or micrococcal nuclease digestion.

22. The method of any one of paragraphs 1 to 21, the method further comprising a step of analyzing the isolated nucleic acid fragments.

23. The method of paragraph 22, wherein analyzing the isolated nucleic acid fragments comprises determining the nucleotide sequence.

24. The method of paragraph 23, wherein the nucleotide sequence is determined using sequencing or hybridization techniques with or without amplification.

25. The method of paragraph 24, wherein the techniques are ChIP-Seq, real-time PCR, DNA microarray, or NANOSTRING® array.

26. A chromatin immunoprecipitation kit for parallel processing of multiple samples in a multi-well format, the kit comprising:
a) a multi-well plate comprising wells coated on an inside surface of the wells with a first affinity molecule that binds to a chromatin-associated factor, or is coated with a molecule that binds to the first affinity molecule, to form a first affinity surface, and
b) a multi-well plate coated with a second affinity molecule that has binds nucleic acids, or is coated with a molecule that binds to the second affinity molecule, to form a second affinity surface,
optionally further comprising a protein inhibitor, a cross-linking solution, a cell lysis buffer, a wash buffer, an elution buffer, and/or user instructions.

27. The chromatin immunoprecipitation kit of paragraph 26, wherein the kit comprises a single multi-well plate that comprises different wells for first and second affinity surfaces.

28. The chromatin immunoprecipitation kit of paragraph 26, wherein the kit comprises a single multi-well plate that comprises wells that have both first and second affinity surfaces.

29. A chromatin immunoprecipitation kit for parallel processing of multiple samples, the kit comprising:
a) a first bead coated with a first affinity molecule that binds to a chromatin-associated factor, or coated with a molecule that binds to the first affinity molecule, to form a first affinity surface, and
b) a second bead coated with a second affinity molecule that binds nucleic acids, or coated with a molecule that binds to the second affinity molecule, to form a second affinity surface,
optionally further comprising a multi-well plate, a protein inhibitor, a cross-linking solution, a cell lysis buffer, a wash buffer, an elution buffer, and/or user instructions.

30. The kit of paragraph 26 or paragraph 29, wherein the second affinity molecule comprises silica.

31. The kit of paragraph 26 or paragraph 29, wherein the second affinity molecule comprises a poly-T oligonucleotide, a poly-A oligonucleotide, avidin, streptavidin or biotin.

32. The kit of paragraph 26, wherein the multi-well plate is a 6-well plate, a 12-well plate, a 24-well plate, a 96-well plate, a 384-well plate or a 1536-well plate.

33. The kit of paragraphs 26 or 29, wherein the molecule that binds to the first affinity molecule comprises protein A or protein G.

34. The kit of paragraphs 26 or 29, wherein the first affinity molecule comprises an antibody that specifically binds to a chromatin-associated factor, an antibody that specifically binds to an affinity tag, avidin, streptavidin or biotin.

35. The kit of paragraph 34, wherein the affinity tag is FLAG-tag, myc-tag, biotin, or DHFR.

36. The kit of paragraph 34, wherein the wherein the antibody is an anti-FLAG antibody, an anti-myc antibody, or an anti-DHFR antibody.

37. The kit of paragraph 29, wherein the bead is a magnetic bead.

38. A method of preparing an indexed sequence library comprising: (a) purifying or obtaining purified ChIP DNA processed using any one of the preceding methods; (b) adding unique sequence identifiers to the purified ChIP DNA; and (c) selecting the ChIP DNA in (b) based on size.

39. The method of paragraph 38, further comprising assessing the ChIP DNA in (c) for enriched molecular binding sites.

40. The method of paragraph 38 or paragraph 39, further comprising sequencing the ChIP DNA.

41. The method of any one of paragraphs 1-25 or 38-40, wherein the method is performed using a multi-well format or a microfluidic chamber/channel.

42. The method of any one of paragraphs 1-25 or 38-40, wherein the library is constructed on magnetic particles.

EXAMPLES

The present invention will be more specifically illustrated by the following examples. However, it should be understood that the present invention is not limited by these examples in any manner. Other examples in accordance with certain aspects and embodiments of the invention are described in international application number PCT/US2011/054072, filed Sep. 29, 2011, which claims the benefit under 35 U.S.C. §119(e) of U.S. provisional application Ser. No. 61/387,689, filed Sep. 29, 2010, each of which is incorporated by reference herein in its entirety.

Example 1

A series of different tissues or cells are subjected to genome-wide mapping of various histone modifications, one of which is histone tri-methylated H3 lysine 4 (H3K4me3). Pre-determined amounts of polypeptide-oligonucleotide conjugates representing either a H3K4me3 histone or an un-methylated histone are "spiked" into each tissue/cell sample prior to immunoprecipitation. The samples are then be subjected to parallel processing and immunoprecipitation. High-throughput sequencing is used to identify the specific genomic sequences enriched and to determine the degree of enrichment across the tissue/cell samples analyzed. The relative ratios of the polypeptide-oligonucleotide conjugates determined in the sequencing step are used to determine the efficiency of H3K4me3 enrichment in each of the parallel assays. This information is used to normalize the signal data across the multiple samples (to account for inherent variation in the immunoprecipitation step), thereby enabling direct comparisons of enrichment values.

Example 2

Four 125 bp DNA strands comprising unique sequences (U) were generated: two complimentary pairs in which the upper strand in each pair was conjugated to either the peptide recognized by an antibody specific for H3K4me3 (Millipore, catalogue Number: 07-473, rabbit, polyclonal) or the same peptide without the methylation modification—as a specificity control, that should not be recognized.

IS (1)

(SEQ ID NO: 73)

ARTK(me3)QTAR

-continued (SEQ ID NO: 74)
-GGC-TGCAGGGACGAGTAGCACATATCGACCAGGAACGAGTAGCACTAG
ACCCACCGGGAGGAGTAGAAGTAGTTCAGGGTGCGGTAGACCCGGATATG
AATGGAGACCCACTACCTCGCGACCGAGGA, (C6-SH
modification added to 60th base);

(2)
(SEQ ID NO: 71)
ARTKQTAR (SEQ ID NO: 72)
-GGC-CTGGCATGCAAGGGGCGGAGGGTGAACGACTAGCACATATCGACC
AGGAACGAGTAGCACTAGACCCACCGGGAGGAGTAGAAGTAGTTCAGGGT
GCGGTGAAACAGGATGTGAACCGCGATCCT, (C6-SH
modification added to 60th base);

(3) No peptide-
(SEQ ID NO: 76)
AGGATCGCGGTTCACATCCTGTTTCACCGCACCCTGAACTACTTCTACTC
CTCCCGGTGGGTCTAGTGCTACTCGTTCCTGGTCGATATGTGCTAGTCGT
TCACCCTCCGCCCCTTGCATGCCAG;
and (4) No peptide-
(SEQ ID NO: 75)
TCCTCGGTCGCGAGGTAGTGGGTCTCCATTCATATCGGGTCTACCGCAC
CCTGAACTACTTCTACTCCTCCCGGTGGGTCTAGTGCTACTCGTTCCTGG
TCGATATGTGCTACTCGTCCCTGCA.

In order to evaluate the efficiency of the internal standard (IS), two ChIP experiments were carried out with either the H3K4me3 (Millipore, catalogue Number: 07-473, rabbit, polyclonal) antibody that should recognize IS (1) or with a non-relevant control antibody that should recognize H3K36me3 (Abcam, catalogue Number: ab9050, rabbit, polyclonal), but none of the IS in this experiment. $3 \times 10^6$ mouse ES cells cross-linked with 1% formaldehyde were lysed and then sonicated using Branson™ sonifier. The samples were then separated into two ChIP experiments-one for each antibody. The two polypeptide-oligonucleotide conjugates were annealed each with the complementary strand and both were spiked to each ChIP. The samples were incubated overnight with the specific antibodies, and the bound fraction was pulled down (immuno-precipitated) and washed according to published protocols, e.g. (Ku M et al. (2008) Genomewide. Analysis of PRC1 and PRC2 Occupancy Identifies Two Classes of Bivalent Domains. PLoS Genet 4(10): e1000242). DNA was purified using QIAGEN MINIELUTE KIT (QIAgen). The specific immunoprecipitation was evaluated using qPCR. Using the primers specific for the H3K4me3-IS: Up primer—TCCTCGGTCGCGAG-GTAGT (SEQ ID NO: 77); Down primer—GTAGTTCA-GGGTGCGGTAGACCCGG (SEQ ID NO: 78), the ratio of H3K4me3-IS immunopercipitated in the ChIP with H3K4me3 antibody was as high as 75-fold over the ChIP performed with the non-relevant antibody specific for H3K36me3. Using the primers that amplify the Control-IS: Up primer—AGGATCGCGGTTCACATCCTGTT (SEQ ID NO: 79); Down primer—CTGGCATG-CAAGGGGCGGA (SEQ ID NO: 80) the ratio between the ChIP performed with the H3K4me3-specific over the ratio in the ChIP performed with the control antibody (H3K36me3) was about 1-showing no specific immunopercipitation. Furthermore, in order to compare between enrichments in two reactions of a given peptide, the ratio of H3K4me3/Control qPCR results from the ChIP performed with H3K4me3 was divided by the results of ChIP performed with the control antibody—H3K36me3. This ratio takes into account the primer efficiency. The resulting enrichment was up to 86-fold of specific immunoprecipitation of the H3K4me3-IS (Table 1).

TABLE 1

|  |  | Pos | Cp |  | K4/K36 | (K4/K36) K4-ChIP/(K4/K36) K36-ChIP |
|---|---|---|---|---|---|---|
| H3_qPCR | K4 | A1 | 20.44 | 20.4 | 1.160704 |  |
|  |  | A2 | 20.41 |  |  |  |
|  | K36 | A3 | 20.27 | 20.6 |  |  |
|  |  | A4 | 21.01 |  |  |  |
| H3K4me3_qPCR | K4 | C1 | 14.71 | 15.0 | 30.90996 | 26.63035951 |
|  |  | C2 | 15.2 |  |  |  |
|  | K36 | C3 | 19.87 | 19.9 |  |  |
|  |  | C4 | 19.94 |  |  |  |
| H3_qPCR_long | K4 | E1 | 20.44 | 20.5 | 0.861546 |  |
|  |  | E2 | 20.5 |  |  |  |
|  | K36 | E3 | 20.6 | 20.3 |  |  |
|  |  | E4 | 19.91 |  |  |  |
| H3K4me3_qPCR_long | K4 | G1 | 15.19 | 15.4 | 37.79177 | 43.86504976 |
|  |  | G2 | 15.59 |  |  |  |
|  | K36 | G3 | 20.37 | 20.6 |  |  |
|  |  | G4 | 20.89 |  |  |  |
| H3_qPCR_short | K4 | I1 | 19.51 | 19.7 | 0.870551 |  |
|  |  | I2 | 19.85 |  |  |  |
|  | K36 | I3 | 19.06 | 19.5 |  |  |
|  |  | I4 | 19.9 |  |  |  |
| H3K4me3_qPCR_short | K4 | K1 | 14.18 | 14.5 | 45.88657 | 52.70982511 |
|  |  | K2 | 14.88 |  |  |  |
|  | K36 | K3 | 19.85 | 20.1 |  |  |
|  |  | K4 | 20.25 |  |  |  |
| H3K4me3_qPCR_Vshort | K4 | M1 | 14.03 | 14.2 | 75.58353 | 86.82267696 |
|  |  | M2 | 14.41 |  |  |  |
|  | K36 | M3 | 20.07 | 20.5 |  |  |
|  |  | M4 | 20.85 |  |  |  |

Example 3

Internal Standards (IS) Protocol

Each internal standards is provided as a 50 µl aliquot of 20 ng IS. The IS is diluted accordingly ($\sim \frac{1}{5} \times 10^4$), and 10-100 femtograms (fg) of IS are added after the sonication procedure. 100 fg allows enrichment with a H3K4me3 antibody at ~cycle 26 of qPCR, while 10 fg yields enrichment at ~cycle 30.

Primers (mixes of either of the two up primers with each of the four down primers, resulting in 8 options). Run qPCR at 65° C. annealing temperature:

```
H3K4me3_qPCR_up_long
                                        (SEQ ID NO: 81)
TCCTCGGTCGCGAGGTAGT H3K4me3_qPCR_up
                                        (SEQ ID NO: 82)
CGCGAGGTAGTGGGTCTC H3K4me3_qPCR_down_long
                                        (SEQ ID NO: 83)
TGCAGGGACGAGTAGCA H3K4me3_qPCR_down
                                        (SEQ ID NO: 84)
ATCGACCAGGAACGAGTAGC H3K4me3_qPCR_down_short
                                        (SEQ ID NO: 85)
CCACCGGGAGGAGTAGAAG H3K4me3_qPCR_down_60bp
                                        (SEQ ID NO: 33)
GTAGTTCAGGGTGCGGTAGACCCGG
```

EQUIVALENTS AND SCOPE

Those skilled in the art will recognize or be able to ascertain using no more than routine experimentation many equivalents to the specific embodiments described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method of validating a chromatin immunoprecipitation (ChIP) assay result, the method comprising:
   (a) obtaining an input sample of the genomic material of interest and of one or more polypeptide-oligonucleotide conjugate of the formula:

A-L-N, wherein A is a polypeptide comprising 5 amino acids, L is a linker and N is an oligonucleotide comprising 10 nucleotides, wherein the sequence of the 10 nucleotides of N uniquely identifies an amino acid sequence and/or amino acid modification of A wherein A comprises an amino acid sequence derived from a histone protein selected from the group consisting of histone HI, H2A, H2AX, H2B, H3 and H4,
   (b) performing a ChIP assay, thereby processing, in parallel to the genomic material of interest of (a), the one or more polypeptide-oligonucleotide conjugates of (a),
   (c) obtaining a processed sample of the polypeptide-oligonucleotide conjugate and the genomic material of interest processed in (b), and
   (d) analyzing the samples obtained in (c), thereby obtaining a value and/or signal for each of the analyzed processed samples, and
   (e) validating the ChIP assay result based on the value and/or signal obtained in (d).

2. The method of claim 1, wherein validating comprises one or more comparisons of the value and/or signal of the input sample and the value and/or signal of the processed sample of C1 with the value and/or signal of the input sample and the value and/or signal of the processed sample of C2, wherein
   (a) C1 is the genomic material of interest and C2 is a polypeptide-oligonucleotide conjugate, wherein C2 is a polypeptide-oligonucleotide conjugate immunoprecipitated with an antibody that is specific for the polypeptide-oligonucleotide conjugate (C2S), or C2 is a polypeptide-oligonucleotide conjugate immunoprecipitated with an antibody that is non-specific for the polypeptide-oligonucleotide conjugate (C2N), and/or
   (b) C1 is a polypeptide-oligonucleotide conjugate immunoprecipitated with an antibody that is specific for the polypeptide-oligonucleotide conjugate and C2 is a polypeptide-oligonucleotide conjugate immunoprecipitated with an antibody that is non-specific for the polypeptide-oligonucleotide conjugate.

3. The method of claim 2, wherein when
(i) the value and/or signal of the processed sample in (a) of C1 and C2S is significantly higher than the value and/or signal of the input sample, then the genomic sample comprises an epitope specific for the antibody that is specific for C2S,
(ii) the value and/or signal of the processed sample in (a) of C1 and C2N is significantly higher than the value and/or signal of the input sample, then the genomic sample is non-specifically amplified and the value or signal obtained is discarded,
(iii) the value and/or signal of the processed sample in (a) of C1 is not significantly higher than the value and/or signal of the input sample and the value and/or signal of the processed sample of C2S is significantly higher than the value and/or signal of the input sample, then the genomic sample does not comprise an epitope specific for the antibody that is specific for C2S,
(iv) the value and/or signal of the processed sample in (a) of C1 is significantly higher than the value and/or signal of the input sample and the value and/or signal of the processed sample of C2S is not significantly higher than the value and/or signal of the input sample, then the genomic sample is non-specifically amplified and the value or signal obtained is discarded,
(v) the value and/or signal of the processed sample in (b) of C1 is significantly higher than the value and/or signal of the input sample and the value and/or signal of the processed sample of C2 is not significantly higher than the value and/or signal of the input sample, then the data obtained is analyzed,
(vi) the value and/or signal of the processed sample in (b) of C1 and C2 is significantly higher than the value and/or signal of the input sample, then the data obtained is not analyzed and is discarded.

4. The method of claim 2, wherein the value and/or signal for the input sample and the processed sample are calculated as ratios.

5. A method of normalizing chromatin immunoprecipitation (ChIP) assay data, the method comprising:
(a) obtaining an input sample of the genomic material of interest and of one or more of polypeptide-oligonucleotide conjugate of the formula:

A-L-N, wherein A is a polypeptide comprising 5 amino acids, L is a linker, and N is an oligonucleotide comprising 10 nucleotides, wherein the sequence of the 10 nucleotides of N uniquely identifies an amino acid sequence and/or amino acid modification of A wherein A comprises an amino acid sequence derived from a histone protein selected from the group consisting of histone HI, H2A, H2AX, H2B, H3 and H4,
(b) performing a ChIP assay, thereby processing, in parallel to the genomic material of interest in (a), the one or more polypeptide-oligonucleotide conjugates of (a),
(c) obtaining a processed sample of the polypeptide-oligonucleotide conjugate and the genomic material of interest processed in (b),
(d) analyzing the samples obtained in (c), thereby obtaining a value and/or signal for each of the analyzed processed samples, and
(e) normalizing the values and/or signals obtained in (d) for each of the processed samples using the values obtained in (d) for each of the input samples.

6. The method of claim 5, wherein parallel processing in (b) comprises contacting the genomic material with the one or more polypeptide-oligonucleotide conjugates.

7. The method of claim 6, wherein the contacting of the genomic material with the one or more polypeptide-oligonucleotide conjugates is performed after fragmentation of the genomic material and before the resulting sample is contacted with an antibody.

8. The method of claim 5, wherein performing a ChIP assay in (b) comprises one or more steps of:
(a) fragmenting genomic material of interest,
(b) contacting the fragmented genomic material and the one or more polypeptide-oligonucleotide conjugates with an antibody,
(c) immobilizing the antibody and specifically bound material,
(d) reducing the amount of non-specifically bound material,
(e) releasing the specifically bound material from the antibody,
(f) reversing a previous cross-linking reaction,
(g) fragmenting proteinaceous material, and/or
(h) purifying nucleic acid material.

9. The method of claim 5, wherein analyzing the processed sample in (d) comprises performing a polymerase-chain reaction, a sequencing reaction, and/or a hybridization reaction.

10. The method of claim 5, wherein normalizing in (e) comprises calculating ratios for input sample and processed sample for the genomic material and the one or more polypeptide-oligonucleotide conjugates.

11. The method of claim 1, wherein A comprises 5 consecutive amino acids derived from any one sequence selected from the group consisting of

```
                                            (SEQ ID NO: 1)
SGRGKQGCKARAK, (SEQ ID NO: 2)
VLLPKKTESHHKAKGK, (SEQ ID NO: 3)
PEPAKSAPAPKKGSKKAVTK, (SEQ ID NO: 4)
AVSEGTKAVTKYTSSK, (SEQ ID NO: 5)
ARTKQTARKSTGGKAPRKQLATKAARKSAPATGGVK, (SEQ ID NO: 6)
QRLVREIAQDFKTDLRFQSSAVMALQEA,
and (SEQ ID NO: 7)
SGRGKGGKGLGKGGAKRHRKVLRDNIQGITKPAIRRLA.
```

12. The method of claim 1, wherein A comprises an amino acid modification.

13. The method of claim 12, wherein the amino acid modification is selected from the group consisting of acetylation, methylation (mono-, di-, tri-), phosphorylation, ubiquitination (mono-, di-, tri-, poly-), sumoylation, ADP-ribosylation, citrullination, biotinylation and cis-trans isomerization.

14. The method of claim 5, wherein A comprises 5 consecutive amino acids derived from any one sequence selected from the group consisting of

```
                              (SEQ ID NO: 1)
SGRGKQGCKARAK, (SEQ ID NO: 2)
VLLPKKTESHHKAKGK, (SEQ ID NO: 3)
PEPAKSAPAPKKGSKKAVTK, (SEQ ID NO: 4)
AVSEGTKAVTKYTSSK, (SEQ ID NO: 5)
ARTKQTARKSTGGKAPRKQLATKAARKSAPATGGVK, (SEQ ID NO: 6)
QRLVREIAQDFKTDLRFQSSAVMALQEA,
and (SEQ ID NO: 7)
SGRGKGGKGLGKGGAKRHRKVLRDNIQGITKPAIRRLA.
```

15. The method of claim 5, wherein A comprises an amino acid modification.

16. The method of claim 15, wherein the amino acid modification is selected from the group consisting of acetylation, methylation (mono-, di-, tri-), phosphorylation, ubiquitination (mono-, di-, tri-, poly-), sumoylation, ADP-ribosylation, citrullination, biotinylation and cis-trans isomerization.

\* \* \* \* \*

UNITED STATES PATENT AND TRADEMARK OFFICE
CERTIFICATE OF CORRECTION

PATENT NO. : 9,631,226 B2  
APPLICATION NO. : 14/855664  
DATED : April 25, 2017  
INVENTOR(S) : Bradley E. Bernstein et al.

Page 1 of 1

It is certified that error appears in the above-identified patent and that said Letters Patent is hereby corrected as shown below:

In the Specification

At Column 1, the "GOVERNMENT SUPPORT" section should be replaced to read as follows: "This invention was made with government support under Grant Nos. U54 HG004570 and U01 ES017155 awarded by the National Institutes of Health. The government has certain rights in the invention."

Signed and Sealed this  
Eighth Day of August, 2017

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 85

<210> SEQ ID NO 1
<211> LENGTH: 13
<212> TYPE: PRT
<213> ORGANISM: Artificial sequence
<220> FEATURE:
<223> OTHER INFORMATION: Synthetic sequence

<400> SEQUENCE: 1
```

-continued

Ser Gly Arg Gly Lys Gln Gly Cys Lys Ala Arg Ala Lys
1               5                   10

<210> SEQ ID NO 2
<211> LENGTH: 16
<212> TYPE: PRT
<213> ORGANISM: Artificial sequence
<220> FEATURE:
<223> OTHER INFORMATION: Synthetic sequence

<400> SEQUENCE: 2

Val Leu Leu Pro Lys Lys Thr Glu Ser His His Lys Ala Lys Gly Lys
1               5                   10                  15

<210> SEQ ID NO 3
<211> LENGTH: 20
<212> TYPE: PRT
<213> ORGANISM: Artificial sequence
<220> FEATURE:
<223> OTHER INFORMATION: Synthetic sequence

<400> SEQUENCE: 3

Pro Glu Pro Ala Lys Ser Ala Pro Ala Pro Lys Lys Gly Ser Lys Lys
1               5                   10                  15

Ala Val Thr Lys
            20

<210> SEQ ID NO 4
<211> LENGTH: 16
<212> TYPE: PRT
<213> ORGANISM: Artificial sequence
<220> FEATURE:
<223> OTHER INFORMATION: Synthetic sequence

<400> SEQUENCE: 4

Ala Val Ser Glu Gly Thr Lys Ala Val Thr Lys Tyr Thr Ser Ser Lys
1               5                   10                  15

<210> SEQ ID NO 5
<211> LENGTH: 36
<212> TYPE: PRT
<213> ORGANISM: Artificial sequence
<220> FEATURE:
<223> OTHER INFORMATION: Synthetic sequence

<400> SEQUENCE: 5

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
                20                  25                  30

Gly Gly Val Lys
            35

<210> SEQ ID NO 6
<211> LENGTH: 28
<212> TYPE: PRT
<213> ORGANISM: Artificial sequence
<220> FEATURE:
<223> OTHER INFORMATION: Synthetic sequence

<400> SEQUENCE: 6

Gln Arg Leu Val Arg Glu Ile Ala Gln Asp Phe Lys Thr Asp Leu Arg
1               5                   10                  15

Phe Gln Ser Ser Ala Val Met Ala Leu Gln Glu Ala
                20                  25

<210> SEQ ID NO 7
<211> LENGTH: 38
<212> TYPE: PRT
<213> ORGANISM: Artificial sequence
<220> FEATURE:
<223> OTHER INFORMATION: Synthetic sequence

<400> SEQUENCE: 7

Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Ile Thr Lys Pro
            20                  25                  30

Ala Ile Arg Arg Leu Ala
        35

<210> SEQ ID NO 8
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MISC_FEATURE
<222> LOCATION: (6)..(6)
<223> OTHER INFORMATION: X is any one or more amino acids

<400> SEQUENCE: 8

Xaa Ser Gly Arg Gly Xaa
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (5)..(5)
<223> OTHER INFORMATION: ACETYLATION
<220> FEATURE:
<221> NAME/KEY: MISC_FEATURE
<222> LOCATION: (9)..(9)
<223> OTHER INFORMATION: X is any one or more amino acids

<400> SEQUENCE: 9

Xaa Gly Arg Gly Lys Gln Gly Cys Xaa
1               5

<210> SEQ ID NO 10
<211> LENGTH: 10
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE

```
<222> LOCATION: (1)..(1)
<223> OTHER INFORMATION: X is any one or more amino acids
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MISC_FEATURE
<222> LOCATION: (10)..(10)
<223> OTHER INFORMATION: X is any one or more amino acids

<400> SEQUENCE: 10

Xaa Ser Gly Arg Gly Lys Gln Gly Cys Xaa
1               5                   10

<210> SEQ ID NO 11
<211> LENGTH: 10
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (6)..(6)
<223> OTHER INFORMATION: ACETYLATION
<220> FEATURE:
<221> NAME/KEY: MISC_FEATURE
<222> LOCATION: (10)..(10)
<223> OTHER INFORMATION: X is any one or more amino acids

<400> SEQUENCE: 11

Xaa Ser Gly Arg Gly Lys Gln Gly Cys Xaa
1               5                   10

<210> SEQ ID NO 12
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (5)..(5)
<223> OTHER INFORMATION: ACETYLATION
<220> FEATURE:
<221> NAME/KEY: misc_feature
<222> LOCATION: (9)..(9)
<223> OTHER INFORMATION: X is any one or more amino acid

<400> SEQUENCE: 12

Xaa Gln Gly Cys Lys Ala Arg Ala Xaa
1               5

<210> SEQ ID NO 13
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
```

-continued

```
<222> LOCATION: (2)..(2)
<223> OTHER INFORMATION: UBIQUITINATION
<220> FEATURE:
<221> NAME/KEY: MISC_FEATURE
<222> LOCATION: (6)..(6)
<223> OTHER INFORMATION: X is any one or more amino acids

<400> SEQUENCE: 13

Xaa Lys Thr Glu Ser Xaa
1               5

<210> SEQ ID NO 14
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MISC_FEATURE
<222> LOCATION: (7)..(7)
<223> OTHER INFORMATION: X is any one or more amino acids

<400> SEQUENCE: 14

Xaa Lys Thr Glu Ser His Xaa
1               5

<210> SEQ ID NO 15
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (2)..(2)
<223> OTHER INFORMATION: UBIQUITINATION
<220> FEATURE:
<221> NAME/KEY: MISC_FEATURE
<222> LOCATION: (7)..(7)
<223> OTHER INFORMATION: X is any one or more amino acids

<400> SEQUENCE: 15

Xaa Lys Thr Glu Ser His Xaa
1               5

<210> SEQ ID NO 16
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MISC_FEATURE
```

```
<222> LOCATION: (7)..(7)
<223> OTHER INFORMATION: X is any one or more amino acids

<400> SEQUENCE: 16

Xaa Lys Thr Glu Ser His Xaa
1               5

<210> SEQ ID NO 17
<211> LENGTH: 15
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: X is any one or more amino acids
<220> FEATURE:
<221> NAME/KEY: misc_feature
<222> LOCATION: (15)..(15)
<223> OTHER INFORMATION: X is any one or more amino acids

<400> SEQUENCE: 17

Xaa Ser Gly Arg Gly Lys Gln Gly Cys Lys Ala Arg Ala Lys Xaa
1               5                   10                  15

<210> SEQ ID NO 18
<211> LENGTH: 18
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: X is any one or more amino acids
<220> FEATURE:
<221> NAME/KEY: misc_feature
<222> LOCATION: (18)..(18)
<223> OTHER INFORMATION: X is any one or more amino acids

<400> SEQUENCE: 18

Xaa Val Leu Leu Pro Lys Lys Thr Glu Ser His His Lys Ala Lys Gly
1               5                   10                  15

Lys Xaa

<210> SEQ ID NO 19
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (6)..(6)
<223> OTHER INFORMATION: ACETYLATION
<220> FEATURE:
<221> NAME/KEY: MISC_FEATURE
<222> LOCATION: (8)..(8)
<223> OTHER INFORMATION: X is any one or more amino acids

<400> SEQUENCE: 19

Xaa Pro Glu Pro Ala Lys Ser Xaa
1               5

<210> SEQ ID NO 20
```

```
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (2)..(2)
<223> OTHER INFORMATION: ACETYLATION
<220> FEATURE:
<221> NAME/KEY: MISC_FEATURE
<222> LOCATION: (7)..(7)
<223> OTHER INFORMATION: X is any one or more amino acids

<400> SEQUENCE: 20

Xaa Lys Gly Ser Lys Lys Xaa
1               5

<210> SEQ ID NO 21
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MISC_FEATURE
<222> LOCATION: (7)..(7)
<223> OTHER INFORMATION: X is any one or more amino acids

<400> SEQUENCE: 21

Xaa Lys Gly Ser Lys Lys Xaa
1               5

<210> SEQ ID NO 22
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (5)..(5)
<223> OTHER INFORMATION: ACETYLATION
<220> FEATURE:
<221> NAME/KEY: MISC_FEATURE
<222> LOCATION: (7)..(7)
<223> OTHER INFORMATION: X is any one or more amino acids

<400> SEQUENCE: 22

Xaa Lys Gly Ser Lys Lys Xaa
1               5

<210> SEQ ID NO 23
<211> LENGTH: 11
<212> TYPE: PRT
<213> ORGANISM: Artificial sequence
<220> FEATURE:
```

```
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (2)..(2)
<223> OTHER INFORMATION: UBIQUITINATION
<220> FEATURE:
<221> NAME/KEY: MISC_FEATURE
<222> LOCATION: (11)..(11)
<223> OTHER INFORMATION: X is any one or more amino acids

<400> SEQUENCE: 23

Xaa Lys Ala Val Thr Lys Tyr Thr Ser Ser Xaa
1               5                   10

<210> SEQ ID NO 24
<211> LENGTH: 12
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (6)..(6)
<223> OTHER INFORMATION: ACETYLATION
<220> FEATURE:
<221> NAME/KEY: MISC_FEATURE
<222> LOCATION: (12)..(12)
<223> OTHER INFORMATION: X is any one or more amino acids

<400> SEQUENCE: 24

Xaa Pro Ala Pro Lys Lys Gly Ser Lys Lys Ala Xaa
1               5                   10

<210> SEQ ID NO 25
<211> LENGTH: 15
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<220> FEATURE:
<221> NAME/KEY: MOD_RES
<222> LOCATION: (9)..(9)
<223> OTHER INFORMATION: ACETYLATION
<220> FEATURE:
<221> NAME/KEY: MISC_FEATURE
<222> LOCATION: (15)..(15)

<400> SEQUENCE: 25

Xaa Pro Ala Pro Lys Lys Gly Ser Lys Lys Ala Val Thr Lys Xaa
1               5                   10                  15

<210> SEQ ID NO 26
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<220> FEATURE:
<221> NAME/KEY: MOD_RES
```

```
<222> LOCATION: (4)..(4)
<223> OTHER INFORMATION: PHOSPHORYLATION
<220> FEATURE:
<221> NAME/KEY: MISC_FEATURE
<222> LOCATION: (7)..(7)

<400> SEQUENCE: 26

Xaa Lys Gly Ser Lys Lys Xaa
1               5

<210> SEQ ID NO 27
<211> LENGTH: 22
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: X is any one or more amino acids
<220> FEATURE:
<221> NAME/KEY: misc_feature
<222> LOCATION: (22)..(22)
<223> OTHER INFORMATION: X is any one or more amino acids

<400> SEQUENCE: 27

Xaa Pro Glu Pro Ala Lys Ser Ala Pro Ala Pro Lys Lys Gly Ser Lys
1               5                   10                  15

Lys Ala Val Thr Lys Xaa
            20

<210> SEQ ID NO 28
<211> LENGTH: 18
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: X is any one or more amino acids
<220> FEATURE:
<221> NAME/KEY: misc_feature
<222> LOCATION: (18)..(18)
<223> OTHER INFORMATION: X is any one or more amino acids

<400> SEQUENCE: 28

Xaa Ala Val Ser Glu Gly Thr Lys Ala Val Thr Lys Tyr Thr Ser Ser
1               5                   10                  15

Lys Xaa

<210> SEQ ID NO 29
<211> LENGTH: 38
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: X is any one or more amino acids
<220> FEATURE:
<221> NAME/KEY: misc_feature
<222> LOCATION: (38)..(38)
<223> OTHER INFORMATION: X is any one or more amino acids

<400> SEQUENCE: 29

Xaa Ala Arg Thr Lys Gln Thr Ala Arg Lys Ser Thr Gly Gly Lys Ala
1               5                   10                  15
```

```
Pro Arg Lys Gln Leu Ala Thr Lys Ala Ala Arg Lys Ser Ala Pro Ala
            20                  25                  30

Thr Gly Gly Val Lys Xaa
        35

<210> SEQ ID NO 30
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acid
<220> FEATURE:
<221> NAME/KEY: MOD_RES
<222> LOCATION: (4)..(4)
<223> OTHER INFORMATION: METHYLATION
<220> FEATURE:
<221> NAME/KEY: misc_feature
<222> LOCATION: (6)..(6)
<223> OTHER INFORMATION: X is any one or more amino acids

<400> SEQUENCE: 30

Xaa Ala Arg Thr Lys Xaa
1               5

<210> SEQ ID NO 31
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MISC_FEATURE
<222> LOCATION: (5)..(5)
<223> OTHER INFORMATION: X is any one or more amino acids

<400> SEQUENCE: 31

Xaa Arg Thr Lys Xaa
1               5

<210> SEQ ID NO 32
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acid
<220> FEATURE:
<221> NAME/KEY: MOD_RES
<222> LOCATION: (5)..(5)
<223> OTHER INFORMATION: METHYLATION
<220> FEATURE:
<221> NAME/KEY: MISC_FEATURE
<222> LOCATION: (9)..(9)
<223> OTHER INFORMATION: X is any one or more amino acid

<400> SEQUENCE: 32

Xaa Ala Arg Thr Lys Gln Thr Ala Xaa
```

```
<210> SEQ ID NO 33
<211> LENGTH: 25
<212> TYPE: PRT
<213> ORGANISM: Artificial sequence
<220> FEATURE:
<223> OTHER INFORMATION: Synthetic sequence

<400> SEQUENCE: 33

Gly Thr Ala Gly Thr Thr Cys Ala Gly Gly Thr Gly Cys Gly Gly
1               5                   10                  15

Thr Ala Gly Ala Cys Cys Cys Gly Gly
            20                  25

<210> SEQ ID NO 34
<211> LENGTH: 13
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (9)..(9)
<223> OTHER INFORMATION: ACETYLATION
<220> FEATURE:
<221> NAME/KEY: MISC_FEATURE
<222> LOCATION: (13)..(13)
<223> OTHER INFORMATION: X is any one or more amino acids

<400> SEQUENCE: 34

Xaa Ala Arg Lys Ser Thr Gly Gly Lys Ala Pro Arg Xaa
1               5                   10

<210> SEQ ID NO 35
<211> LENGTH: 17
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (9)..(9)
<223> OTHER INFORMATION: METHYLATION
<220> FEATURE:
<221> NAME/KEY: MISC_FEATURE
<222> LOCATION: (17)..(17)
<223> OTHER INFORMATION: X is any one or more amino acids

<400> SEQUENCE: 35

Xaa Ala Arg Thr Lys Gln Thr Ala Arg Lys Ser Thr Gly Gly Lys Ala
1               5                   10                  15

Xaa

<210> SEQ ID NO 36
<211> LENGTH: 11
<212> TYPE: PRT
<213> ORGANISM: Artificial sequence
```

```
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MISC_FEATURE
<222> LOCATION: (11)..(11)
<223> OTHER INFORMATION: X is any one or more amino acids

<400> SEQUENCE: 36

Xaa Arg Lys Ser Thr Gly Gly Lys Ala Pro Xaa
1               5                   10

<210> SEQ ID NO 37
<211> LENGTH: 38
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: X is any one or more amino acids
<220> FEATURE:
<221> NAME/KEY: misc_feature
<222> LOCATION: (38)..(38)
<223> OTHER INFORMATION: X is any one or more amino acids

<400> SEQUENCE: 37

Xaa Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Xaa
        35

<210> SEQ ID NO 38
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (6)..(6)
<223> OTHER INFORMATION: X is any one or more amino acids

<400> SEQUENCE: 38

Xaa Arg Lys Ser Ala Xaa
1               5

<210> SEQ ID NO 39
<211> LENGTH: 8
```

```
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (4)..(4)
<223> OTHER INFORMATION: METHYLATION
<220> FEATURE:
<221> NAME/KEY: MISC_FEATURE
<222> LOCATION: (8)..(8)
<223> OTHER INFORMATION: X is any one or more amino acids

<400> SEQUENCE: 39

Xaa Ala Arg Lys Ser Ala Pro Xaa
1               5

<210> SEQ ID NO 40
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (3)..(3)
<223> OTHER INFORMATION: ACETYLATION
<220> FEATURE:
<221> NAME/KEY: MISC_FEATURE
<222> LOCATION: (6)..(6)
<223> OTHER INFORMATION: X is any one or more amino acids

<400> SEQUENCE: 40

Xaa Arg Lys Ser Ala Xaa
1               5

<210> SEQ ID NO 41
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MISC_FEATURE
<222> LOCATION: (6)..(6)
<223> OTHER INFORMATION: X is any one or more amino acids

<400> SEQUENCE: 41

Xaa Ser Ala Pro Ala Xaa
1               5

<210> SEQ ID NO 42
<211> LENGTH: 30
<212> TYPE: PRT
<213> ORGANISM: Artificial sequence
<220> FEATURE:
<223> OTHER INFORMATION: Synthetic sequence
```

```
<220> FEATURE:
<221> NAME/KEY: misc_feature
<222> LOCATION: (1)..(1)
<223> OTHER INFORMATION: X is any one or more amino acids
<220> FEATURE:
<221> NAME/KEY: misc_feature
<222> LOCATION: (30)..(30)
<223> OTHER INFORMATION: X is any one or more amino acids

<400> SEQUENCE: 42

Xaa Gln Arg Leu Val Arg Glu Ile Ala Gln Asp Phe Lys Thr Asp Leu
1               5                   10                  15

Arg Phe Gln Ser Ser Ala Val Met Ala Leu Gln Glu Ala Xaa
            20                  25                  30

<210> SEQ ID NO 43
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (4)..(4)
<223> OTHER INFORMATION: METHYLATION
<220> FEATURE:
<221> NAME/KEY: MISC_FEATURE
<222> LOCATION: (7)..(7)
<223> OTHER INFORMATION: X is any one or more amino acids

<400> SEQUENCE: 43

Xaa Asp Phe Lys Thr Asp Xaa
1               5

<210> SEQ ID NO 44
<211> LENGTH: 11
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (11)..(11)
<223> OTHER INFORMATION: X is any one or more amino acids

<400> SEQUENCE: 44

Xaa Lys Thr Asp Leu Arg Phe Gln Ser Ser Xaa
1               5                   10

<210> SEQ ID NO 45
<211> LENGTH: 38
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acid
<220> FEATURE:
```

```
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION
<220> FEATURE:
<221> NAME/KEY: MISC_FEATURE
<222> LOCATION: (38)..(38)
<223> OTHER INFORMATION: X is any one or more amino acid

<400> SEQUENCE: 45

Xaa Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
                20                  25                  30

Thr Gly Gly Val Lys Xaa
        35

<210> SEQ ID NO 46
<211> LENGTH: 13
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (9)..(9)
<223> OTHER INFORMATION: ACETYLATION
<220> FEATURE:
<221> NAME/KEY: MISC_FEATURE
<222> LOCATION: (13)..(13)
<223> OTHER INFORMATION: X is any one or more amino acids

<400> SEQUENCE: 46

Xaa Ala Arg Lys Ser Thr Gly Gly Lys Ala Pro Arg Xaa
1               5                   10

<210> SEQ ID NO 47
<211> LENGTH: 12
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (9)..(9)
<223> OTHER INFORMATION: METHYLATION
<220> FEATURE:
<221> NAME/KEY: MISC_FEATURE
<222> LOCATION: (12)..(12)
<223> OTHER INFORMATION: X is any one or more amino acids

<400> SEQUENCE: 47

Xaa Arg Thr Lys Gln Thr Ala Arg Lys Ser Thr Xaa
```

```
<210> SEQ ID NO 48
<211> LENGTH: 32
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is a any one or more amino acids
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (8)..(8)
<223> OTHER INFORMATION: METHYLATION
<220> FEATURE:
<221> NAME/KEY: MOD_RES
<222> LOCATION: (26)..(26)
<223> OTHER INFORMATION: METHYLATION
<220> FEATURE:
<221> NAME/KEY: MISC_FEATURE
<222> LOCATION: (32)..(32)
<223> OTHER INFORMATION: X is a any one or more amino acids

<400> SEQUENCE: 48

Xaa Thr Lys Gln Thr Ala Arg Lys Ser Thr Gly Gly Lys Ala Pro Arg
1               5                   10                  15

Lys Gln Leu Ala Thr Lys Ala Ala Arg Lys Ser Ala Pro Ala Thr Xaa
            20                  25                  30

<210> SEQ ID NO 49
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MISC_FEATURE
<222> LOCATION: (5)..(5)
<223> OTHER INFORMATION: X is any one or more amino acids

<400> SEQUENCE: 49

Xaa Ser Gly Arg Xaa
1               5

<210> SEQ ID NO 50
<211> LENGTH: 40
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (4)..(4)
<223> OTHER INFORMATION: METHYLATION
<220> FEATURE:
```

```
<221> NAME/KEY: MISC_FEATURE
<222> LOCATION: (40)..(40)
<223> OTHER INFORMATION: X is any one or more amino acids

<400> SEQUENCE: 50

Xaa Ser Gly Arg Gly Lys Gly Gly Lys Gly Leu Gly Lys Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Xaa
        35                  40

<210> SEQ ID NO 51
<211> LENGTH: 10
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (6)..(6)
<223> OTHER INFORMATION: ACETYLATION
<220> FEATURE:
<221> NAME/KEY: MISC_FEATURE
<222> LOCATION: (10)..(10)
<223> OTHER INFORMATION: X is any one or more amino acids

<400> SEQUENCE: 51

Xaa Ser Gly Arg Gly Lys Gly Gly Lys Xaa
1               5                   10

<210> SEQ ID NO 52
<211> LENGTH: 25
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (9)..(9)
<223> OTHER INFORMATION: ACETYLATION
<220> FEATURE:
<221> NAME/KEY: MISC_FEATURE
<222> LOCATION: (25)..(25)
<223> OTHER INFORMATION: X is any one or more amino acids

<400> SEQUENCE: 52

Xaa Ser Gly Arg Gly Lys Gly Gly Lys Gly Leu Gly Lys Gly Gly Ala
1               5                   10                  15

Lys Arg His Arg Lys Val Leu Arg Xaa
            20                  25

<210> SEQ ID NO 53
<211> LENGTH: 16
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
```

```
<220> FEATURE:
<221> NAME/KEY: MOD_RES
<222> LOCATION: (10)..(10)
<223> OTHER INFORMATION: ACETYLATION
<220> FEATURE:
<221> NAME/KEY: MISC_FEATURE
<222> LOCATION: (16)..(16)
<223> OTHER INFORMATION: X is any one or more amino acids

<400> SEQUENCE: 53

Xaa Gly Lys Gly Gly Lys Gly Leu Gly Lys Gly Gly Ala Lys Arg Xaa
1               5                   10                  15

<210> SEQ ID NO 54
<211> LENGTH: 23
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (7)..(7)
<223> OTHER INFORMATION: ACETYLATION
<220> FEATURE:
<221> NAME/KEY: MISC_FEATURE
<222> LOCATION: (23)..(23)
<223> OTHER INFORMATION: X is any one or more amino acids

<400> SEQUENCE: 54

Xaa Gly Lys Gly Gly Ala Lys Arg His Arg Lys Val Leu Arg Asp Asn
1               5                   10                  15

Ile Gln Gly Ile Thr Lys Xaa
            20

<210> SEQ ID NO 55
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (5)..(5)
<223> OTHER INFORMATION: X is any one or more amino acids

<400> SEQUENCE: 55

Xaa Lys Val Leu Xaa
1               5

<210> SEQ ID NO 56
<211> LENGTH: 26
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
```

```
<221> NAME/KEY: MOD_RES
<222> LOCATION: (14)..(14)
<223> OTHER INFORMATION: METHYLATION
<220> FEATURE:
<221> NAME/KEY: MISC_FEATURE
<222> LOCATION: (26)..(26)
<223> OTHER INFORMATION: X is any one or more amino acids

<400> SEQUENCE: 56

Xaa Lys Gly Leu Gly Lys Gly Gly Ala Lys Arg His Arg Lys Val Leu
1               5                   10                  15

Arg Asp Asn Ile Gln Gly Ile Thr Lys Xaa
            20                  25

<210> SEQ ID NO 57
<211> LENGTH: 40
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: X is any one or more amino acids
<220> FEATURE:
<221> NAME/KEY: misc_feature
<222> LOCATION: (40)..(40)
<223> OTHER INFORMATION: X is any one or more amino acids

<400> SEQUENCE: 57

Xaa Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Xaa
        35                  40

<210> SEQ ID NO 58
<211> LENGTH: 19
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (5)..(5)
<223> OTHER INFORMATION: ACETYLATION
<220> FEATURE:
<221> NAME/KEY: MOD_RES
<222> LOCATION: (12)..(12)
<223> OTHER INFORMATION: ACETYLATION
<220> FEATURE:
<221> NAME/KEY: MISC_FEATURE
<222> LOCATION: (19)..(19)
<223> OTHER INFORMATION: X is any one or more amino acids

<400> SEQUENCE: 58

Xaa Gly Arg Gly Lys Gly Gly Lys Gly Leu Gly Lys Gly Gly Ala Lys
1               5                   10                  15

Arg His Xaa

<210> SEQ ID NO 59
<211> LENGTH: 15
<212> TYPE: PRT
<213> ORGANISM: Artificial sequence
```

```
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X is any one or more amino acids
<220> FEATURE:
<221> NAME/KEY: MOD_RES
<222> LOCATION: (4)..(4)
<223> OTHER INFORMATION: ACETYLATION
<220> FEATURE:
<221> NAME/KEY: MOD_RES
<222> LOCATION: (12)..(12)
<223> OTHER INFORMATION: ACETYLATION
<220> FEATURE:
<221> NAME/KEY: MISC_FEATURE
<222> LOCATION: (15)..(15)
<223> OTHER INFORMATION: X is any one or more amino acids

<400> SEQUENCE: 59

Xaa Gly Gly Lys Gly Leu Gly Lys Gly Gly Ala Lys Arg His Xaa
1               5                   10                  15

<210> SEQ ID NO 60
<211> LENGTH: 30
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (6)..(6)
<223> OTHER INFORMATION: PHOSPHORYLATION

<400> SEQUENCE: 60

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn
            20                  25                  30

<210> SEQ ID NO 61
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: PHOSPHORYLATION

<400> SEQUENCE: 61

Pro Gln Ser Asp Pro Ser
1               5

<210> SEQ ID NO 62
<211> LENGTH: 12
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (2)..(2)
<223> OTHER INFORMATION: PHOSPHORYLATION

<400> SEQUENCE: 62

Gln Ser Asp Pro Ser Val Glu Pro Pro Leu Ser Gln
1               5                   10
```

```
<210> SEQ ID NO 63
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (6)..(6)
<223> OTHER INFORMATION: PHOSPHORYLATION

<400> SEQUENCE: 63

Met Glu Glu Pro Gln Ser Asp
1               5

<210> SEQ ID NO 64
<211> LENGTH: 33
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (13)..(13)
<223> OTHER INFORMATION: ACETYLATION

<400> SEQUENCE: 64

Gly Ser Arg Ala His Ser Ser His Leu Lys Ser Lys Lys Gly Gln Ser
1               5                   10                  15

Thr Ser Arg His Lys Lys Leu Met Phe Lys Thr Glu Gly Pro Asp Ser
            20                  25                  30

Asp

<210> SEQ ID NO 65
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: ACETYLATION

<400> SEQUENCE: 65

Ser Lys Lys Gly Gln
1               5

<210> SEQ ID NO 66
<211> LENGTH: 13
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (6)..(6)
<223> OTHER INFORMATION: ACETYLATION

<400> SEQUENCE: 66

His Leu Lys Ser Lys Lys Gly Gln Ser Thr Ser Arg His
1               5                   10

<210> SEQ ID NO 67
<211> LENGTH: 2
<212> TYPE: PRT
<213> ORGANISM: Artificial sequence
<220> FEATURE:
<223> OTHER INFORMATION: Synthetic sequence
```

```
<220> FEATURE:
<221> NAME/KEY: MOD_RES
<222> LOCATION: (1)..(1)
<223> OTHER INFORMATION: ACETYLATION

<400> SEQUENCE: 67

Lys Gly
1

<210> SEQ ID NO 68
<211> LENGTH: 60
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (33)..(33)
<223> OTHER INFORMATION: ACETYLATION
<220> FEATURE:
<221> NAME/KEY: MOD_RES
<222> LOCATION: (34)..(34)
<223> OTHER INFORMATION: ACETYLATION

<400> SEQUENCE: 68

Thr Ser Glu Lys Phe Gln Lys Ile Asn Gln Met Val Cys Asn Ser Asp
1               5                   10                  15

Arg Val Leu Lys Arg Ser Ala Glu Gly Ser Asn Pro Lys Pro Leu
            20                  25                  30

Lys Lys Leu Arg Phe Asp Ile Glu Gly Ser Asp Glu Ala Asp Gly Ser
        35                  40                  45

Lys His Leu Pro Gly Glu Ser Lys Phe Gln Gln Lys
    50                  55                  60

<210> SEQ ID NO 69
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (3)..(3)
<223> OTHER INFORMATION: ACETYLATION
<220> FEATURE:
<221> NAME/KEY: MOD_RES
<222> LOCATION: (4)..(4)
<223> OTHER INFORMATION: ACETYLATION

<400> SEQUENCE: 69

Pro Leu Lys Lys Leu Arg Phe Asp
1               5

<210> SEQ ID NO 70
<211> LENGTH: 21
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (6)..(6)
<223> OTHER INFORMATION: ACETYLATION
<220> FEATURE:
<221> NAME/KEY: MOD_RES
<222> LOCATION: (7)..(7)
<223> OTHER INFORMATION: ACETYLATION

<400> SEQUENCE: 70
```

```
Pro Pro Lys Pro Leu Lys Lys Leu Arg Phe Asp Ile Glu Gly Ser Asp
1               5                   10                  15

Glu Ala Asp Gly Ser
            20

<210> SEQ ID NO 71
<211> LENGTH: 8
<212> TYPE: PRT
<213> ORGANISM: Artificial sequence
<220> FEATURE:
<223> OTHER INFORMATION: Synthetic sequence

<400> SEQUENCE: 71

Ala Arg Thr Lys Gln Thr Ala Arg
1               5

<210> SEQ ID NO 72
<211> LENGTH: 128
<212> TYPE: DNA
<213> ORGANISM: Artificial sequence
<220> FEATURE:
<223> OTHER INFORMATION: Synthetic sequence

<400> SEQUENCE: 72
ggcctggcat gcaagggcg gagggtgaac gactagcaca tatcgaccag gaacgagtag      60
cactagaccc accgggagga gtagaagtag ttcagggtgc ggtgaaacag gatgtgaacc    120
gcgatcct                                                            128

<210> SEQ ID NO 73
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MOD_RES
<222> LOCATION: (4)..(4)
<223> OTHER INFORMATION: METHYLATION

<400> SEQUENCE: 73

Ala Arg Thr Lys Gln Thr Ala Arg
1               5

<210> SEQ ID NO 74
<211> LENGTH: 128
<212> TYPE: DNA
<213> ORGANISM: Artificial sequence
<220> FEATURE:
<223> OTHER INFORMATION: Synthetic sequence

<400> SEQUENCE: 74
ggctgcaggg acgagtagca catatcgacc aggaacgagt agcactagac ccaccgggag     60
gagtagaagt agttcagggt gcggtagacc cggatatgaa tggagaccca ctacctcgcg   120
accgagga                                                            128

<210> SEQ ID NO 75
<211> LENGTH: 125
<212> TYPE: DNA
<213> ORGANISM: Artificial sequence
<220> FEATURE:
<223> OTHER INFORMATION: Synthetic sequence

<400> SEQUENCE: 75
tcctcggtcg cgaggtagtg ggtctccatt catatccggg tctaccgcac cctgaactac     60
```
ttctactcct cccggtgggt ctagtgctac tcgttcctgg tcgatatgtg ctactcgtcc    120
ctgca    125

<210> SEQ ID NO 76
<211> LENGTH: 125
<212> TYPE: DNA
<213> ORGANISM: Artificial sequence
<220> FEATURE:
<223> OTHER INFORMATION: Synthetic sequence

<400> SEQUENCE: 76
aggatcgcgg ttcacatcct gtttcaccgc accctgaact acttctactc ctcccggtgg    60
gtctagtgct actcgttcct ggtcgatatg tgctagtcgt tcaccctccg cccttgcat    120 gccag    125

<210> SEQ ID NO 77
<211> LENGTH: 19
<212> TYPE: DNA
<213> ORGANISM: Artificial sequence
<220> FEATURE:
<223> OTHER INFORMATION: Synthetic sequence

<400> SEQUENCE: 77
tcctcggtcg cgaggtagt    19

<210> SEQ ID NO 78
<211> LENGTH: 25
<212> TYPE: DNA
<213> ORGANISM: Artificial sequence
<220> FEATURE:
<223> OTHER INFORMATION: Synthetic sequence

<400> SEQUENCE: 78
gtagttcagg gtgcggtaga cccgg    25

<210> SEQ ID NO 79
<211> LENGTH: 23
<212> TYPE: DNA
<213> ORGANISM: Artificial sequence
<220> FEATURE:
<223> OTHER INFORMATION: Synthetic sequence

<400> SEQUENCE: 79
aggatcgcgg ttcacatcct gtt    23

<210> SEQ ID NO 80
<211> LENGTH: 19
<212> TYPE: DNA
<213> ORGANISM: Artificial sequence
<220> FEATURE:
<223> OTHER INFORMATION: Synthetic sequence

<400> SEQUENCE: 80
ctggcatgca aggggcgga    19

<210> SEQ ID NO 81
<211> LENGTH: 19
<212> TYPE: DNA
<213> ORGANISM: Artificial sequence
<220> FEATURE:
<223> OTHER INFORMATION: Synthetic sequence

<400> SEQUENCE: 81

```
tcctcggtcg cgaggtagt                                          19

<210> SEQ ID NO 82
<211> LENGTH: 18
<212> TYPE: DNA
<213> ORGANISM: Artificial sequence
<220> FEATURE:
<223> OTHER INFORMATION: Synthetic sequence

<400> SEQUENCE: 82
cgcgaggtag tgggtctc                                           18

<210> SEQ ID NO 83
<211> LENGTH: 17
<212> TYPE: DNA
<213> ORGANISM: Artificial sequence
<220> FEATURE:
<223> OTHER INFORMATION: Synthetic sequence

<400> SEQUENCE: 83
tgcagggacg agtagca                                            17

<210> SEQ ID NO 84
<211> LENGTH: 20
<212> TYPE: DNA
<213> ORGANISM: Artificial sequence
<220> FEATURE:
<223> OTHER INFORMATION: Synthetic sequence

<400> SEQUENCE: 84
atcgaccagg aacgagtagc                                         20

<210> SEQ ID NO 85
<211> LENGTH: 19
<212> TYPE: DNA
<213> ORGANISM: Artificial sequence
<220> FEATURE:
<223> OTHER INFORMATION: Synthetic sequence

<400> SEQUENCE: 85
ccaccgggag gagtagaag                                          19
```